US010617890B2

(12) United States Patent
Mazin et al.

(10) Patent No.: US 10,617,890 B2
(45) Date of Patent: Apr. 14, 2020

(54) SYSTEMS AND METHODS FOR USE IN EMISSION GUIDED RADIATION THERAPY

(71) Applicant: RefleXion Medical, Inc., Hayward, CA (US)

(72) Inventors: Samuel Mazin, Menlo Park, CA (US); Akshay Nanduri, San Francisco, CA (US)

(73) Assignee: RefleXion Medical, Inc., Hayward, CA (US)

( * ) Notice: Subject to any disclaimer, the term of this patent is extended or adjusted under 35 U.S.C. 154(b) by 0 days.

(21) Appl. No.: 16/193,725

(22) Filed: Nov. 16, 2018

(65) Prior Publication Data
US 2019/0083815 A1    Mar. 21, 2019

Related U.S. Application Data

(62) Division of application No. 15/684,693, filed on Aug. 23, 2017, now Pat. No. 10,143,857, which is a
(Continued)

(51) Int. Cl.
*A61N 5/10* (2006.01)
*A61B 6/12* (2006.01)
(Continued)

(52) U.S. Cl.
CPC ............ *A61N 5/1065* (2013.01); *A61B 5/055* (2013.01); *A61B 6/032* (2013.01); *A61B 6/037* (2013.01);
(Continued)

(58) Field of Classification Search
CPC ...... A61N 5/1064; A61N 5/1081; A61N 5/10; A61N 5/1039; G01T 1/2985; G01T 1/2907
See application file for complete search history.

(56) References Cited

U.S. PATENT DOCUMENTS

| 3,794,840 A | 2/1974 | Scott |
| 3,906,233 A | 9/1975 | Vogel |

(Continued)

FOREIGN PATENT DOCUMENTS

| CN | 1681436 A | 10/2005 |
| CN | 1960780 A | 5/2007 |

(Continued)

OTHER PUBLICATIONS

Chang, J.Y. et al. (2008). "Image-Guided Radiation Therapy for Non-Small Cell Lung Cancer," *J. Thorac. Oncol.* FEB 3(2):177-186.

(Continued)

*Primary Examiner* — Marcus H Taningco
(74) *Attorney, Agent, or Firm* — Cooley LLP

(57) ABSTRACT

Described herein are systems and methods for positioning a radiation source with respect to one or more regions of interest in a coordinate system. Such systems and methods may be used in emission guided radiation therapy (EGRT) for the localized delivery of radiation to one or more patient tumor regions. These systems comprise a gantry movable about a patient area, where a plurality of positron emission detectors, a radiation source are arranged movably on the gantry, and a controller. The controller is configured to identify a coincident positron annihilation emission path and to position the radiation source to apply a radiation beam along the identified emission path. The systems and methods described herein can be used alone or in conjunction with surgery, chemotherapy, and/or brachytherapy for the treatment of tumors.

10 Claims, 29 Drawing Sheets

Related U.S. Application Data division of application No. 15/499,671, filed on Apr. 27, 2017, now Pat. No. 9,764,161, which is a division of application No. 15/047,552, filed on Feb. 18, 2016, now Pat. No. 9,649,509, which is a division of application No. 14/007,312, filed as application No. PCT/US2012/031704 on Mar. 30, 2012, now Pat. No. 9,283,403.

(60) Provisional application No. 61/470,432, filed on Mar. 31, 2011.

(51) Int. Cl.
 G01T 1/29 (2006.01)
 A61B 6/03 (2006.01)
 A61B 6/00 (2006.01)
 A61B 5/055 (2006.01)
 A61B 90/00 (2016.01)

(52) U.S. Cl.
 CPC .............. *A61B 6/12* (2013.01); *A61B 6/469* (2013.01); *A61B 6/54* (2013.01); *A61N 5/1039* (2013.01); *A61N 5/1042* (2013.01); *A61N 5/1048* (2013.01); *A61N 5/1067* (2013.01); *A61N 5/1081* (2013.01); *G01T 1/2907* (2013.01); *G01T 1/2985* (2013.01); *A61B 2090/374* (2016.02); *A61B 2090/3762* (2016.02); *A61N 5/1001* (2013.01); *A61N 5/1045* (2013.01); *A61N 2005/1074* (2013.01); *A61N 2005/1087* (2013.01)

(56) References Cited

U.S. PATENT DOCUMENTS

| | | | |
|---|---|---|---|
| 4,389,569 A | 6/1983 | Hattori et al. |
| 4,503,331 A | 3/1985 | Kovacs, Jr. et al. |
| 4,529,882 A | 7/1985 | Lee |
| 4,563,582 A | 1/1986 | Mullani |
| 4,575,868 A | 3/1986 | Ueda et al. |
| 4,642,464 A | 2/1987 | Muhani |
| 4,647,779 A | 3/1987 | Wong |
| 4,677,299 A | 6/1987 | Wong |
| 4,868,844 A | 9/1989 | Nunan |
| 5,075,554 A | 12/1991 | Yunker et al. |
| 5,206,512 A | 4/1993 | Iwao |
| 5,207,223 A | 5/1993 | Adler |
| 5,317,616 A | 5/1994 | Swerdloff et al. |
| 5,329,567 A | 7/1994 | Ikebe |
| 5,351,280 A | 9/1994 | Swerdloff et al. |
| 5,390,225 A | 2/1995 | Hawman |
| 5,394,452 A | 2/1995 | Swerdloff et al. |
| 5,396,534 A | 3/1995 | Thomas |
| 5,418,827 A | 5/1995 | Deasy et al. |
| 5,442,675 A | 8/1995 | Swerdloff et al. |
| 5,618,902 A | 4/1997 | Wengrovius et al. |
| 5,647,663 A | 7/1997 | Holmes |
| 5,751,781 A | 5/1998 | Brown et al. |
| 5,813,985 A | 9/1998 | Carroll |
| 5,851,182 A | 12/1998 | Sahadevan |
| 5,937,028 A | 8/1999 | Tybinkowski et al. |
| 6,180,943 B1 | 1/2001 | Lange |
| 6,184,530 B1 | 2/2001 | Hines et al. |
| 6,188,748 B1 | 2/2001 | Pastyr et al. |
| 6,239,438 B1 | 5/2001 | Schubert |
| 6,260,005 B1 | 7/2001 | Yang et al. |
| 6,281,505 B1 | 8/2001 | Hines et al. |
| 6,385,288 B1 | 5/2002 | Kanematsu |
| 6,438,202 B1 | 8/2002 | Olivera et al. |
| 6,449,331 B1 | 9/2002 | Nutt et al. |
| 6,449,340 B1 | 9/2002 | Tybinkowski et al. |
| 6,455,656 B2 | 9/2002 | Gagnon |
| 6,473,634 B1 | 10/2002 | Barni |
| 6,504,899 B2 | 1/2003 | Pugachev et al. |
| 6,552,693 B1 | 4/2003 | Leisten |
| 6,560,311 B1 | 5/2003 | Shepard et al. |
| 6,618,467 B1 | 9/2003 | Ruchala et al. |
| 6,661,866 B1 | 12/2003 | Limkeman et al. |
| 6,696,694 B2 | 2/2004 | Pastyr et al. |
| 6,700,949 B2 | 3/2004 | Susami et al. |
| 6,714,620 B2 | 3/2004 | Caflisch et al. |
| 6,730,924 B1 | 5/2004 | Pastyr et al. |
| 6,735,277 B2 | 5/2004 | McNutt et al. |
| 6,794,653 B2 | 9/2004 | Wainer et al. |
| 6,810,103 B1 | 10/2004 | Tybinkowski et al. |
| 6,831,961 B1 | 12/2004 | Tybinkowski et al. |
| 6,865,254 B2 | 3/2005 | Näfstadius |
| 6,888,919 B2 | 5/2005 | Graf |
| 6,914,959 B2 | 7/2005 | Bailey et al. |
| 6,934,363 B2 | 8/2005 | Seufert |
| 6,965,661 B2 | 11/2005 | Kojima et al. |
| 6,976,784 B2 | 12/2005 | Kojima et al. |
| 6,990,175 B2 | 1/2006 | Nakashima et al. |
| 7,020,233 B1 | 3/2006 | Tybinkowski et al. |
| 7,026,622 B2 | 4/2006 | Kojima et al. |
| 7,110,808 B2 | 9/2006 | Adair |
| 7,154,096 B2 | 12/2006 | Amano |
| 7,167,542 B2 | 1/2007 | Juschka et al. |
| 7,199,382 B2 | 4/2007 | Rigney et al. |
| 7,227,925 B1 | 6/2007 | Mansfield et al. |
| 7,242,750 B2 | 7/2007 | Tsujita |
| 7,263,165 B2 | 8/2007 | Ghelmansarai |
| 7,265,356 B2 | 9/2007 | Pelizzari et al. |
| 7,280,633 B2 | 10/2007 | Cheng et al. |
| 7,291,840 B2 | 11/2007 | Fritzler et al. |
| 7,297,958 B2 | 11/2007 | Kojima et al. |
| 7,298,821 B2 | 11/2007 | Ein-Gal |
| 7,310,410 B2 | 12/2007 | Sohal et al. |
| 7,386,099 B1 | 6/2008 | Kasper et al. |
| 7,397,901 B1 | 7/2008 | Johnsen |
| 7,397,902 B2 | 7/2008 | Seeber et al. |
| 7,453,983 B2 | 11/2008 | Schildkraut et al. |
| 7,453,984 B2 | 11/2008 | Chen et al. |
| 7,469,035 B2 | 12/2008 | Keall et al. |
| 7,555,103 B2 | 6/2009 | Johnsen |
| 7,558,378 B2 | 7/2009 | Juschka et al. |
| 7,560,698 B2 | 7/2009 | Rietzel |
| 7,564,951 B2 | 7/2009 | Hasegawa et al. |
| 7,596,209 B2 | 9/2009 | Perkins |
| 7,627,082 B2 | 12/2009 | Kojima et al. |
| 7,639,853 B2 | 12/2009 | Olivera et al. |
| 7,656,999 B2 | 2/2010 | Hui et al. |
| 7,715,606 B2 | 5/2010 | Jeung et al. |
| 7,742,575 B2 | 6/2010 | Bourne |
| 7,755,055 B2 | 7/2010 | Schilling |
| 7,755,057 B2 | 7/2010 | Kim |
| 7,778,691 B2 | 8/2010 | Zhang et al. |
| 7,792,252 B2 | 9/2010 | Bohn |
| 7,795,590 B2 | 9/2010 | Takahashi et al. |
| 7,839,972 B2 | 11/2010 | Ruchala et al. |
| 7,957,507 B2 | 6/2011 | Cadman |
| 7,965,819 B2 | 6/2011 | Nagata |
| 7,983,380 B2 | 7/2011 | Guertin et al. |
| 8,017,915 B2 | 9/2011 | Mazin |
| 8,059,782 B2 | 11/2011 | Brown |
| 8,063,376 B2 | 11/2011 | Maniawski et al. |
| 8,116,427 B2 | 2/2012 | Kojima et al. |
| 8,139,713 B2 | 3/2012 | Janbakhsh |
| 8,139,714 B1 | 3/2012 | Sahadevan |
| 8,144,962 B2 | 3/2012 | Busch et al. |
| 8,148,695 B2 | 4/2012 | Takahashi et al. |
| 8,232,535 B2 | 7/2012 | Olivera et al. |
| 8,280,002 B2 | 10/2012 | Bani-Hashemi et al. |
| 8,295,906 B2 | 10/2012 | Saunders et al. |
| 8,304,738 B2 | 11/2012 | Gagnon et al. |
| 8,335,296 B2 | 12/2012 | Dehler et al. |
| 8,357,903 B2 | 1/2013 | Wang et al. |
| 8,384,049 B1 | 2/2013 | Broad |
| 8,406,844 B2 | 3/2013 | Ruchala et al. |
| 8,442,287 B2 | 5/2013 | Fordyce, II et al. |
| 8,461,538 B2 | 6/2013 | Mazin |
| 8,461,539 B2 | 6/2013 | Yamaya et al. |
| 8,483,803 B2 | 7/2013 | Partain et al. |

(56) References Cited

U.S. PATENT DOCUMENTS

| | | |
|---|---|---|
| 8,536,547 B2 | 9/2013 | Maurer, Jr. et al. |
| 8,537,373 B2 | 9/2013 | Humphrey |
| 8,581,196 B2 | 11/2013 | Yamaya et al. |
| 8,588,367 B2 | 11/2013 | Busch et al. |
| 8,617,422 B2 | 12/2013 | Koschan et al. |
| 8,664,610 B2 | 3/2014 | Chuang |
| 8,664,618 B2 | 3/2014 | Yao |
| 8,712,012 B2 | 4/2014 | O'Connor |
| 8,748,825 B2 | 6/2014 | Mazin |
| 8,767,917 B2 | 7/2014 | Ruchala et al. |
| 9,205,281 B2 | 12/2015 | Mazin |
| 9,283,403 B2 | 3/2016 | Mazin et al. |
| 9,649,509 B2 | 5/2017 | Mazin et al. |
| 9,694,208 B2 | 7/2017 | Mazin et al. |
| 9,731,148 B2 | 8/2017 | Olivera et al. |
| 9,764,161 B2 | 9/2017 | Mazin et al. |
| 9,820,700 B2 | 11/2017 | Mazin |
| 10,143,857 B2 | 12/2018 | Mazin et al. |
| 10,159,852 B2 | 12/2018 | Mazin et al. |
| 10,327,716 B2 | 6/2019 | Mazin |
| 2002/0051513 A1 | 5/2002 | Pugachev et al. |
| 2002/0163994 A1 | 11/2002 | Jones |
| 2002/0191734 A1 | 12/2002 | Kohima et al. |
| 2002/0193685 A1 | 12/2002 | Mate et al. |
| 2003/0036700 A1 | 2/2003 | Weinberg |
| 2003/0128801 A1 | 7/2003 | Eisenberg et al. |
| 2003/0219098 A1 | 11/2003 | McNutt |
| 2004/0024300 A1 | 2/2004 | Graf |
| 2004/0030246 A1 | 2/2004 | Townsend et al. |
| 2004/0057557 A1 | 3/2004 | Nafstadius |
| 2004/0158416 A1 | 8/2004 | Slates |
| 2006/0002511 A1 | 1/2006 | Miller et al. |
| 2006/0113482 A1 | 6/2006 | Pelizzari et al. |
| 2006/0173294 A1 | 8/2006 | Ein-Gal |
| 2006/0182326 A1 | 8/2006 | Schildkraut et al. |
| 2006/0193435 A1 | 8/2006 | Hara et al. |
| 2006/0237652 A1 | 10/2006 | Kimchy |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0043289 A1 | 2/2007 | Adair |
| 2007/0053491 A1 | 3/2007 | Schildkraut et al. |
| 2007/0055144 A1 | 3/2007 | Neustadter et al. |
| 2007/0211857 A1 | 9/2007 | Urano et al. |
| 2007/0221869 A1 | 9/2007 | Song |
| 2007/0265528 A1 | 11/2007 | Xu et al. |
| 2008/0002811 A1 | 1/2008 | Allison |
| 2008/0031404 A1 | 2/2008 | Khamene et al. |
| 2008/0128631 A1 | 6/2008 | Suhami |
| 2008/0130825 A1 | 6/2008 | Fu et al. |
| 2008/0152085 A1 | 6/2008 | Saracen et al. |
| 2008/0156993 A1 | 7/2008 | Weinberg et al. |
| 2008/0205588 A1 | 8/2008 | Kim |
| 2008/0230705 A1 | 9/2008 | Rousso et al. |
| 2008/0253516 A1 | 10/2008 | Hui et al. |
| 2008/0273659 A1 | 11/2008 | Guertin et al. |
| 2008/0298536 A1 | 12/2008 | Ein-Gal |
| 2009/0003655 A1 | 1/2009 | Wollenweber |
| 2009/0086909 A1 | 4/2009 | Hui et al. |
| 2009/0116616 A1 | 5/2009 | Lu et al. |
| 2009/0169082 A1 | 7/2009 | Mizuta et al. |
| 2009/0256078 A1 | 10/2009 | Mazin |
| 2010/0040197 A1 | 2/2010 | Maniawski et al. |
| 2010/0054412 A1 | 3/2010 | Brinks et al. |
| 2010/0067660 A1 | 3/2010 | Maurer, Jr. et al. |
| 2010/0069742 A1 | 3/2010 | Partain et al. |
| 2010/0074408 A1 | 3/2010 | Bert et al. |
| 2010/0166274 A1 | 7/2010 | Busch et al. |
| 2011/0006212 A1 | 1/2011 | Shchory et al. |
| 2011/0044429 A1 | 2/2011 | Takahashi et al. |
| 2011/0073763 A1 | 3/2011 | Subbarao |
| 2011/0092814 A1 | 4/2011 | Yamaya et al. |
| 2011/0272600 A1 | 11/2011 | Bert et al. |
| 2011/0301449 A1 | 12/2011 | Maurer, Jr. |
| 2011/0309255 A1 | 12/2011 | Bert et al. |
| 2011/0313231 A1 | 12/2011 | Guertin et al. |
| 2012/0230464 A1 | 9/2012 | Ling et al. |
| 2013/0266116 A1 | 10/2013 | Abenaim et al. |
| 2014/0107390 A1 | 4/2014 | Brown et al. |
| 2014/0239204 A1 | 8/2014 | Orton et al. |
| 2017/0368372 A1 | 12/2017 | Mazin et al. |
| 2018/0001109 A1 | 1/2018 | Mazin et al. |
| 2018/0110483 A1 | 4/2018 | Mazin |
| 2019/0001152 A1 | 1/2019 | O'Connor et al. |
| 2019/0118001 A1 | 4/2019 | Mazin et al. |

FOREIGN PATENT DOCUMENTS

| | | |
|---|---|---|
| CN | 101970043 A | 2/2011 |
| DE | 10 2008 053321 A1 | 5/2010 |
| EP | 2 188 815 B1 | 5/2010 |
| EP | 2 687 259 A1 | 1/2014 |
| JP | 09-33658 A | 2/1997 |
| JP | 9-189769 A2 | 7/1997 |
| JP | 2000-105279 A | 4/2000 |
| JP | 2001-340474 A | 12/2001 |
| JP | 2002-534823 A | 10/2002 |
| JP | 2003-534823 A | 11/2003 |
| JP | 2004-513735 A | 5/2004 |
| JP | 2006-145281 A | 6/2006 |
| JP | 2007-502166 A | 2/2007 |
| JP | 2007-507246 A | 3/2007 |
| JP | 2008-173299 A | 7/2008 |
| JP | 2011-514213 A | 5/2011 |
| WO | WO-89/10090 A1 | 11/1989 |
| WO | WO-2000/015299 A1 | 3/2000 |
| WO | WO-2004/017832 A2 | 3/2004 |
| WO | WO-2004/017832 A3 | 3/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/110495 A1 | 11/2005 |
| WO | WO-2007/045076 A1 | 4/2007 |
| WO | WO-2007/124760 A1 | 11/2007 |
| WO | WO-2008/019118 A2 | 2/2008 |
| WO | WO-2008/024463 A2 | 2/2008 |
| WO | WO-2008/024463 A3 | 2/2008 |
| WO | WO-2009/111580 A2 | 9/2009 |
| WO | WO-2009/111580 A3 | 9/2009 |
| WO | WO-2009/114117 A2 | 9/2009 |
| WO | WO-2010/015358 A1 | 2/2010 |
| WO | WO-2012/135771 A1 | 10/2012 |

OTHER PUBLICATIONS

Chinese First Office Action, dated Sep. 6, 2015, for Chinese Patent Application No. 201280025934X, filed on Mar. 30, 2012, 20 pages (with English Translation).

Erdi, Y.E. (Feb. 2007). "The Use of PET for Radiotherapy," *Current Medical Imaging Reviews* 3(1):3-16.

Extended European Search Report dated Oct. 7. 2015, for European Application No. 12763280.0, filed on Mar. 30, 2012, 11 pages.

Extended European Search Report dated Mar. 31, 2017, for European Application No. 09 719 473.2, filed on Mar. 9, 2009, 8 pages.

Extended European Search Report dated Nov. 21, 2018, for European Application No. 18 168 947.2, filed on Mar. 30, 2012, 8 pages.

Fan, Q. (Nov. 2012). "Emission Guided Radiation Therapy for Lung and Prostate Cancers: A Feasibility Study on a Digital Patient," *Med. Phys.* 39(11):7140-7152.

Fan, Q. et al. (Aug. 2013), "Towards a Planning Scheme for Emission Guided Radiation Therapy (EGRT): FDG Based Tumor Tracking in a Metastatic Breast Cancer Patient," *Med. Phys.* 40(8): 12 pages.

Final Office Action dated Aug. 15, 2012, for U.S. Appl. No. 13/209,275, filed Aug. 12 2011 8 pages.

Final Office Action dated Aug. 2, 2018, for U.S. Appl. No. 15/684,710, filed Aug. 23, 2017, 8 pages.

International Search Report dated May 4, 2009, for PCT Patent Application No. PCT/US09/01500, filed on Mar. 9, 2009, 3 pages.

(56) References Cited

OTHER PUBLICATIONS

International Search Report dated Jul. 20, 2012, for PCT Patent Application No. PCT/US12/31704, filed on Mar. 30, 2012. 3 pages.
Japanese Office Action dated Dec. 25, 2015, for Japanese Patent Application No. 2014-502881 filed Mar. 20, 2012, 14 pages.
Krouglicof, N. et al. (Nov. 2013). "Development of a Novel PCB-Based Voice Coil Actuator for Opto-Mechatronic Applications," *presented at IEEE/RSJ International Conference on Intelligent Robots and Systems (IROS)*, Tokyo, Japan, Nov. 3-7, 2013, pp. 5834-5840.
Lu, W. (2008), "Real-time motion-adaptive delivery (MAD) using binary MLC: I. Static beam (topotherapy) delivery," Phys. Med. Biol, 53:6491-6511.
Lu, W. (2009). "Real-time motion-adaptive-optimization (MAO) in tomotherapy," Phys. Med. Biol. 54:4373-4398.
Mackie, T.R. et al. (Nov.-Dec. 1993). "Tomotherapy: A New Concept for the Delivery of Dynamic Conformal Radiotherapy," *Med. Phys.* 20(6):1709-1719.
Mazin, S.R. et al. (Dec. 2010). "Emission-Guided Radiation Therapy: Biologic Targeting and Adaptive Treatment," *Journal of American College of Radiology* 7(12):989-990.
McMahon, R. et al, (2008), "A real-time dynamic-MLC control algorithm for delivering IMRT to targets undergoing 2D rigid motion in the beam's eye view," Med. Phys. 35:3875-3888.
Non-Final Office Action dated Feb. 24, 2017, for U.S. Appl. No. 15/069,390, filed Mar. 14, 2016, 6 pages.
Non-Final Office Action dated Jan. 10, 2011, for U.S. Appl. No. 12/367,679, filed Feb. 9, 2009, 9 pages.
Non-Final Office Action dated Feb. 28, 2012, for U.S. Appl. No. 13/209,275, filed Aug. 12, 2011, 8 pages.
Non-Final Office Action dated Sep. 19, 2013, for U.S. Appl. No. 13/895,255, filed May 15, 2013, 8 pages.
Non-Final Office Action dated Feb. 21, 2018, for U.S. Appl. No. 15/684,710, filed Aug. 23, 2017, 10 pages.
Non-Final Office Action dated Mar. 27, 2018, for U.S. Appl. No. 15/684,693, filed Aug. 23, 2017, 7 pages.
Notice of Allowance dated Jul. 25, 2011, for U.S. Appl. No. 12/367,679, filed Feb. 9, 2009, 7 pages.
Notice of Allowance dated Apr. 9, 2014, for U.S. Appl. No. 13/895,255, filed May 15, 2013, 7 pages.
Notice of Allowance dated Oct. 27, 2015, for U.S. Appl. No. 14/278,973, filed May 15, 2014, 8 pages.
Notice of Allowance dated Mar. 27, 2013, for U.S. Appl. No. 13/209,275, filed Aug. 12, 2011, 9 pages.
Notice of Allowance dated May 18, 2017, for U.S. Appl. No. 15/069,390, filed Mar. 14, 2016, 5 pages.
Notice of Allowance dated Jul. 19, 2017, for U.S. Appl. No. 15/499,671, filed Apr. 27, 2017, 8 pages.
Notice of Allowance dated Oct. 3, 2018, for U.S. Appl. No. 15/684,693, filed Aug. 23, 2017, 5 pages.
Notice of Allowance dated Oct. 25, 2018, for U.S. Appl. No. 15/684,710, filed Aug. 23, 2017, 7 pages.
Notice of Allowance dated Apr. 4, 2019, for U.S. Appl. No. 15/807,383, filed Nov. 8, 2017, 11 pages.
Olivera, G.H. et al. (2000). "Modifying a plan delivery without re-optimization to account for patient offset in tomotherapy," Proceedings of the $22^{nd}$ Annual EMBS International Conference, Jul. 23-28, 2000, Chicago, IL, pp. 441-444.
Prabhaker, R. et al, (2007, e-published Jan. 2008). "An Insight into PET-CT Based Radiotherapy Treatment Planning," *Cancer Therapy* (5):519-524.
Tashima, H. et al. (Jul. 21, 2012), "A Single-Ring OpenPET Enabling PET Imaging During Radiotherapy." *Phys. Med. Biol.* 57(14):4705-4718.
The Partial Supplementary European Search Report, dated Jun. 25, 2015 for European Application No. 12763280.0, filed on Mar. 30, 2012, 6 pages.
Varian Medical Systems (2004), "Dynamic Targeting™ Image-Guided Radiation Therapy—A Revolution in Cancer Care," *Business Briefing: US Oncology Review*, Abstract only, 2 pages.
Written Opinion dated May 4, 2009, for PCT Patent Application No. PCT/US09/01500, filed on Mar. 9, 2009, 5 pages.
Written Opinion dated Jul. 20, 2012, for PCT Patent Application No. PCT/US12/31704, filed on Mar. 30. 2012, 10 pages.
Yamaya, T. et al, (Jan. 14, 2008), "A Proposal of an Open PET Geometry," *Physics in Medicine and Biology* 53:757-773.
Bangert, M. et al. (2016). "Accelerated iterative beam angle selection in IMRT," Medical Physics 43.3:1073-1082.
Chen, X. et al. (2012). "Smoothing proximal gradient method for general structured sparse regression," The Annals of Applied Statistics 6:719-752.
Extended European Search Report dated Oct. 15, 2019, for European Application No. 17 764 132.1, filed on Mar. 9, 2017, 4 pages.
International Search Report dated Jun. 27, 2017, for PCT Patent Application No. PCT/US2017/021647, filed on Mar. 9, 2017, 3 pages.
Lee, S. et al. (2015). "Treatment plan comparison of Linac step and shoot, tomotherapy, RapidArc, and proton therapy for prostate cancer using dosimetrical and biological index," J. Korean Physical Society 67:7-16 (with tables 1-5), 28 total pages.
Non-Final Office Action dated Sep. 19, 2019, for U.S. Appl. No. 16/217,417, filed Dec. 12, 2018, 7 pages.
Notice of Allowance dated Oct. 5, 2017, for U.S. Appl. No. 14/951,194, filed Nov. 24, 2015, 11 pages.
Written Opinion of the International Searching Authority dated Jun. 27, 2017, for PCT Patent Application No. PCT/US2017/021647, filed on Mar. 9, 2017, 5 pages.

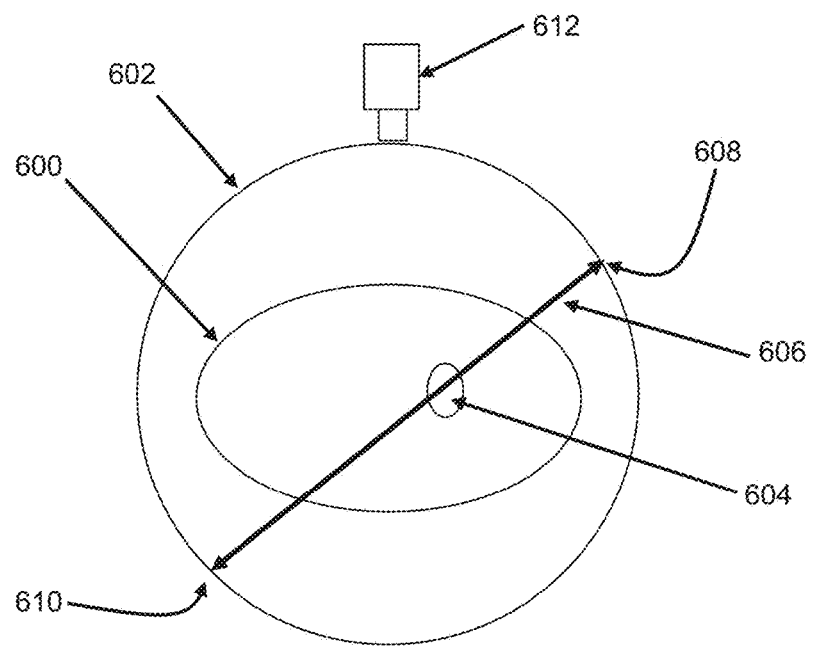
FIG. 6A
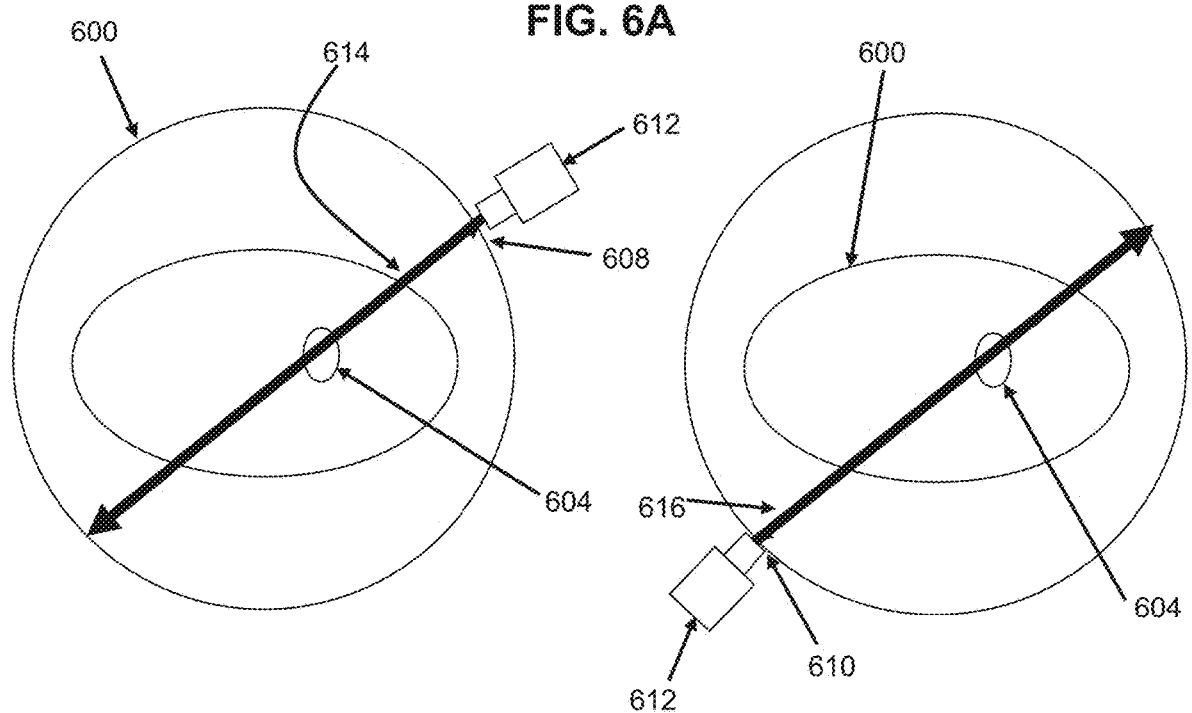
FIG. 6B  FIG. 6C

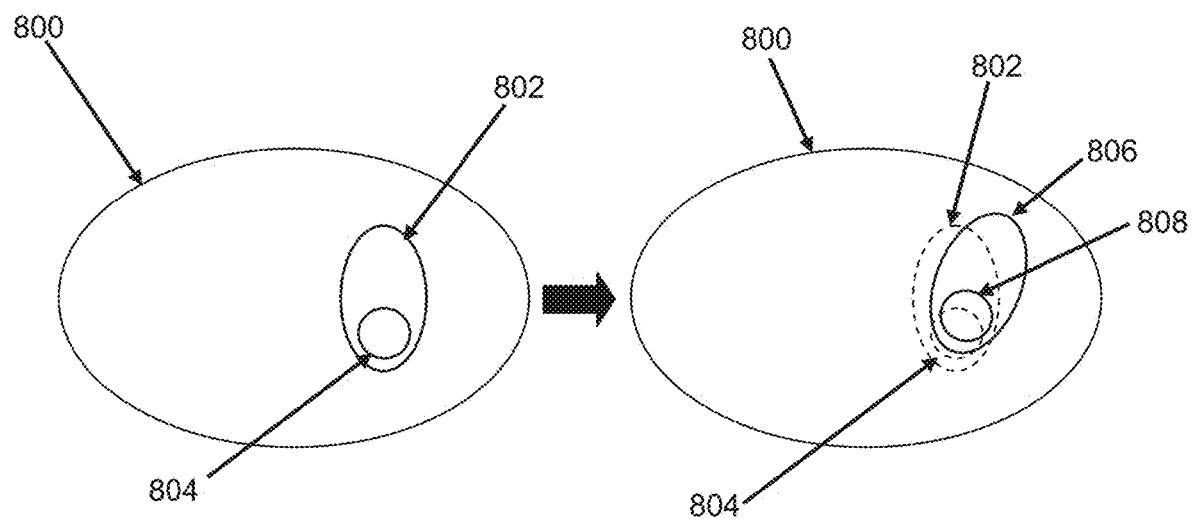

SYSTEMS AND METHODS FOR USE IN EMISSION GUIDED RADIATION THERAPY

CROSS-REFERENCE TO RELATED APPLICATIONS

This application is a divisional of U.S. patent application Ser. No. 15/684,693, filed on Aug. 23, 2017, now issued as U.S. Pat. No. 10,143,857, which is a divisional of U.S. patent application Ser. No. 15/499,671, filed on Apr. 27, 2017, now issued as U.S. Pat. No. 9,764,161, which is a divisional of U.S. patent application Ser. No. 15/047,552, filed on Feb. 18, 2016, now issued as U.S. Pat. No. 9,649,509, which is a divisional of U.S. patent application Ser. No. 14/007,312, filed on Mar. 25, 2014, now issued as U.S. Pat. No. 9,283,403, which has a 371(c) date of Mar. 25, 2014 and adopts the international filing date of Mar. 30, 2012, which is a U.S. National Phase application under 35 U.S.C. § 371 of International Application No. PCT/US2012/031704, filed Mar. 30, 2012, which designated the United States and which claims priority to U.S. Provisional Patent Application No. 61/470,432, filed on Mar. 31, 2011, the disclosures of all of which are hereby incorporated by reference in their entirety.

BACKGROUND

Radiation therapy involves delivering tumoricidal doses of radiation to localized regions of the body. Stereotactic radiation therapy, also called radiosurgery, may be used to treat tumors in the brain, breast, head, neck, lung, liver, pancreas, spine, and prostate. Various tumor localization techniques may be used to precisely determine the location of tumor(s) to help ensure that a high dose of radiation is delivered to the tumor(s), while sparing healthy, non-cancerous tissue. For example, on-board imaging technologies such as single and stereoscopic x-ray imaging, kilovoltage and megavoltage CT imaging, implantable fiducial markers and transponders, ultrasound imaging, MRI, and others may help to improve the efficacy of radiation therapy by gathering tumor location information such that a radiation beam may be specifically targeted at the tumor region. Various radiation beam-shaping techniques may also be used to help direct radiation precisely at the tumor(s) to be treated, while reducing the radiation exposure to surrounding tissue.

BRIEF SUMMARY

Described herein are systems and methods for positioning a radiation source with respect to one or more regions of interest in a coordinate system. In some variations, such systems and methods may be used for emission guided radiation therapy (EGRT) for the localized delivery of radiation to one or more patient tumor regions. EGRT systems may comprise a gantry movable about a patient area, where one or more positron emission detectors and radiation sources are arranged movably on the gantry. The EGRT system may comprise a controller configured to identify a coincident positron annihilation emission path and to direct the radiation source to apply a radiation beam along the identified emission path. Various methods may be used with an EGRT system to regulate the radiation beam that is applied to the target region(s) such that radiation is delivered to the target region(s) while reducing or avoiding the delivery of radiation to other tissue regions. The EGRT systems and methods described herein may be used alone or in conjunction with surgery, chemotherapy, and/or brachytherapy for the treatment of tumors.

One example of an EGRT system described herein may comprise a gantry movable about a patient area, one or more positron emission detectors, one or more therapeutic radiation sources, a motion system, and a microprocessor. Some variations of EGRT systems may comprise one or more single-photon emission detectors. The therapeutic radiation sources may be one or more radioactive materials, x-ray source(s), or particle beam source(s). The positron emission detectors and the therapeutic radiation sources may be positioned at various locations around the gantry for the detection of coincident positron annihilation emission paths that intersect with a target region and the application of radiation beams to deliver a prescribed radiation close to the target region. The radiation beams may be applied along the emission paths and/or at a target location determined based on the detected emissions. The movable gantry may adjust the position of the positron emission detectors and/or therapeutic radiation sources such that various regions of tissue may be treated within the patient area.

The methods described herein may be used with an EGRT system to regulate the radiation beam that is applied to the target region(s) in order to deliver radiation to the target region(s) while reducing or avoiding the delivery of radiation to other tissue regions. For example, EGRT methods may be used to deliver a prescribed dose of radiation to a target volume while avoiding the delivery of radiation to radiation-sensitive structures, compensate for PET signal and/or radiation beam attenuation, collect real-time tumor location data, and perform other functions to help ensure that a tumoricidal level of radiation is delivered to the target volume while preserving surrounding tissue. The EGRT systems and methods described herein may be used alone or in conjunction with surgery, chemotherapy, radiosensitizers, and/or brachytherapy for the treatment of tumors. For example, EGRT systems and methods may be used before and/or after chemotherapy. EGRT may also be used before and/or after surgery and/or brachytherapy. Some variations of tumor treatment plans may comprise surgically removing a portion of the tumor, and treating any remaining tumor masses with chemotherapy and/or EGRT. The various therapies in a tumor treatment plan may be determined in part by the size, type, location, progression and etiology of the tumor(s), as well as a variety of patient variables (e.g., gender, age, allergies, tolerance to certain pharmacological agents, etc.).

One example of a method for emission guided radiation therapy for a target region of tissue may comprise detecting a single coincident positron annihilation emission path that intersects both a target tissue and a radiation-sensitive tissue to be spared using a positron emission detector, and selectively applying radiation along the emission path such that radiation applied to the target tissue is greater than radiation applied to the tissue to be spared. In some variations, applying the radiation along the emission path may comprise emitting radiation in a probabilistic manner, or emitting radiation that has been intensity-modulated in a probabilistic manner.

Another example of an EGRT method for applying radiation to a targeted region of tissue may comprise detecting a single coincident positron annihilation emission path that intersects a target tissue region using a positron emission detector, determining whether the emission path intersects an organ structure, positioning a radiation source to apply radiation along the emission path, and applying radiation along the emission path, where the radiation has been modified by a probabilistic coefficient. In some variations, applying radiation may comprise applying radiation where the intensity of the radiation has been scaled by the probabilistic coefficient.

Another method for EGRT of a target region of tissue may comprise detecting a single coincident positron annihilation emission path that intersects a target region of tissue, where the emission path is substantially perpendicular to a predetermined margin of extension from the target tissue, and applying a radiation beam to the target tissue along the emission path using a radiation source, where a width of the radiation beam may correspond to a width of the margin of extension. In some variations, the target tissue is a PET-avid tissue and the margin of extension may comprise tissue adjacent to the PET-avid tissue.

Another method for EGRT of a target region of tissue may comprise detecting boundaries of a PET-avid region of tissue using a positron emission detector, defining an extension region beyond the boundaries of the PET-avid region, detecting a single coincident positron annihilation emission path that intersects with a selected region of tissue, where the detected emission path may be substantially perpendicular to an axis of the extension region and applying a radiation beam along the detected emission path that may have a width that corresponds to a width of the extension region. In some variations, the positron emission detector may be configured to determine the boundaries of the PET-avid region of tissue region based on the detected positron annihilation emission paths.

Another method for EGRT of a target region of tissue may comprise detecting boundaries of a PET-avid region of tissue using a positron emission detector that is configured to determine the boundaries of the PET-avid region of tissue, defining an extension region beyond the boundaries of the PET-avid region detecting a single coincident positron annihilation emission path that intersects with a selected region of tissue, where the detected emission path may be substantially perpendicular to an axis of the extension region, and applying a radiation beam along the detected emission path that has a width that may correspond to a width of the extension region. In some variations, defining an extension region may comprise using an image obtained by one or more of computed tomography, magnetic resonance imaging, PET, or any other suitable imaging modality.

Another example of a method for EGRT of a target region of tissue may comprise detecting a single coincident positron annihilation emission path using a positron emission detector, where the emission path may intersect a first PET-avid region of tissue to be spared and a second PET-avid region of tissue to be treated, positioning a radiation source at a location from which the radiation source may be capable of applying radiation along the emission path, and applying radiation along the emission path, where the radiation may be adjusted according to a modulation factor that is inversely proportional to a projection of the first PET-avid region of tissue on the location of the radiation source. In some variations, applying radiation may comprise applying radiation beams with a time duration that is modified by the modulation factor. Alternatively or additionally, applying radiation may comprise applying radiation with an intensity that is modified by the modulation factor. In other variations, the second PET-avid region of tissue may intersect with a target region of tissue, and the first region of tissue may not intersect with the target region of tissue.

Yet another method for EGRT of a target region of tissue may comprise detecting a single coincident positron annihilation emission path using a positron emission detector, where the emission path intersects a targeted region of tissue, and applying radiation along the emission path using a radiation source, where the radiation applied may be adjusted according to the total attenuation of the detected positron annihilation emission along the complete emission path as may be determined by an alternate imaging modality. In some variations, the applied radiation may be adjusted according to the attenuation of the therapeutic radiation along the positron annihilation emission path. For example, the applied radiation may be directly proportional or inversely proportional to the attenuation of the detected positron annihilation emission. Examples of alternate imaging modalities may include computed tomography, magnetic resonance imaging, x-ray, and/or any suitable imaging modality.

Another example of a method for EGRT may comprise detecting a single positron annihilation emission path using a positron emission detector, where the emission path intersects a target region of tissue, computing an attenuation factor of the emission path using an image of the target region of tissue acquired by a selected imaging modality, and applying radiation along the emission path, where the radiation is modulated by the attenuation factor. In some variations, the radiation may be adjusted to compensate for the attenuation of the radiation along the positron annihilation emission path. The applied radiation may be proportional or inversely proportional to the attenuation of the detected positron annihilation emission. In some variations, the selected imaging modality may be computed tomography. In some variations, the intensity of the radiation may be modulated proportionally or inversely proportionally to the attenuation factor. Additionally or alternatively, the applied radiation may have a time duration that may be modulated proportionally or inversely proportionally to the attenuation factor. For example, the radiation applied along the emission path may have a frequency that may be modulated inversely proportionally to the attenuation factor.

One variation of a system for EGRT may comprise a gantry movable about a patient area, where the gantry comprises a rotatable inner gantry and a rotatable outer gantry, a plurality of positron emission detectors arranged movably along the inner gantry configured to detect a plurality of positron annihilation emission paths within the patient area, and a radiation source arranged movably along on the outer gantry, wherein the radiation source is configured to apply radiation along each of the plurality of positron annihilation emission paths within the patient area. In some EGRT systems, the inner gantry may be capable of rotating at a higher rate than the outer gantry. In some variations, the system may comprise a sense mode where the plurality of positron emission detectors obstructs the radiation source, and a firing mode where the radiation source is unobstructed and is able to apply radiation to the patient area. Alternatively or additionally, the EGRT system may comprise one or more single photon emission detectors arranged movably along the inner gantry. In some variations, the radiation source may also comprise a collimator.

An example of a method for emission guided radiation therapy may comprise detecting a positron annihilation emission path that intersects with a plurality of target tissue regions using a plurality of positron emission detectors, positioning a radiation source to apply radiation along each of the plurality of emission paths, and applying radiation along each of the emission paths to deliver radiation to the plurality of target tissue regions.

Another example of a system for EGRT may comprise a gantry movable about a patient area, where the gantry comprises a rotatable inner gantry and a rotatable outer gantry, a plurality of positron emission detectors arranged movably along the inner gantry configured to detect a plurality of positron annihilation emission paths from a plurality of moving PET-avid regions within the patient area, and a radiation source arranged movably along on the outer gantry, where the radiation source may be configured to apply radiation to each of the plurality of PET-avid regions within the patient area. In some EGRT systems, the inner gantry may be capable of rotating at a higher rate than the outer gantry. In some variations, the EGRT system may comprise a sense mode where the plurality of positron emission detectors obstructs the radiation source, and a firing mode where the radiation source is unobstructed and is able to apply radiation to the patient area. Alternatively or additionally, the EGRT system may comprise one or more single photon emission detectors arranged movably along the inner gantry. In some variations, the radiation source may also comprise a collimator.

An example of a method for EGRT may comprise detecting a positron annihilation emission path that intersects with a plurality of moving target tissue regions using a plurality of positron emission detectors, positioning a radiation source to apply radiation along the emission path, and applying radiation to the plurality of moving target tissue regions along a path derived from shifting the detected emission path according to the movement of the target tissue regions.

Also described herein are systems that may be used for positioning a radiation source (such as a radiation source that may be used in a system for EGRT). One variation of a system for positioning a radiation source may comprise a circular gantry, a radiation source mounted on the gantry, positron emission detectors mounted on the gantry, and a controller in communication with the radiation source and the positron emission detectors. The positron emission detectors may be configured to detect a positron emission path originating from a first region of interest within a coordinate system and the controller may be configured (e.g., by programming an algorithm that is stored in memory) to position the radiation source along the emission path. The radiation source may be configured (e.g., by a program stored in memory and/or one or more signals from the controller) to generate radiation according to a selected probabilistic coefficient. In some variations, the controller may be configured to determine whether the emission path intersects a second region of interest within the coordinate system, and the radiation source may be configured to generate radiation along the emission path according to the selected probabilistic coefficient if the emission path intersects the second region of interest. Alternatively or additionally, the radiation source may be configured to generate radiation along the emission path if the emission path intersects the second region of interest and the selected probabilistic coefficient is below a pre-programmed probability threshold. In some variations, the radiation source may be configured to generate radiation that has been intensity-modulated in a probabilistic manner along the emission path, and/or may be configured to generate radiation that has been scaled by the probabilistic coefficient.

Another variation of a system for positioning a radiation source may comprise a circular gantry, a radiation source mounted on the gantry, positron emission detectors mounted on the gantry, and a controller in communication with the radiation source and the positron emission detectors. The positron emission detectors may be configured to detect multiple positron emission paths originating from a plurality of regions of interest within a coordinate system and the controller may be configured (e.g., by programming an algorithm that is stored in memory) to position the radiation source along the multiple emission paths.

Another variation of a system for positioning a radiation source may comprise a circular gantry, a radiation source mounted on the gantry, positron emission detectors mounted on the gantry, and a controller in communication with the radiation source and the positron emission detectors. The positron emission detectors may be configured to detect a positron emission path that intersects a plurality of moving regions of interest within a coordinate system and the controller may be configured (e.g., by programming an algorithm that is stored in memory) to position the radiation source along a path derived by shifting the detected emission path according to the movement of the regions of interest.

One variation of a system for positioning a radiation source may comprise a circular gantry, a radiation source mounted on the gantry, positron emission detectors mounted on the gantry, and a controller in communication with the radiation source and the positron emission detectors. The positron emission detectors may be configured detect to a positron emission path that intersects a region of interest within a coordinate system, where the emission path may be substantially perpendicular to a pre-determined direction of margin of extension from the region of interest. The controller may be configured (e.g., by programming an algorithm that is stored in memory) to position the radiation source along the emission path, and the radiation source may be configured (e.g., by a program stored in memory and/or one or more signals from the controller) to generate a radiation beam with a width that corresponds to a width of the margin of extension. In some variations, the region of interest may be PET-avid and the margin of extension may comprise a region adjacent to the PET-avid region of interest.

One variation of a system for positioning a radiation source may comprise a circular gantry, a radiation source mounted on the gantry, positron emission detectors mounted on the gantry, and a controller in communication with the radiation source and the positron emission detectors. The positron emission detectors may be configured to detect boundaries of a PET-avid region of interest within a coordinate system and to detect a single coincident positron annihilation emission path that intersects with a second region of interest within the coordinate system. The controller may be configured (e.g., by programming an algorithm that is stored in memory) to define an extension region beyond the boundaries of the PET-avid legion of interest and to determine whether the detected emission path is substantially perpendicular to an axis of the extension region, and to position the radiation source along the emission path. The radiation source may be configured (e.g., by a program stored in memory and/or one or more signals from the controller) to generate a radiation beam with a width that corresponds to a width of the extension region. In some examples, the controller may be configured to define an extension region by using an image obtained by computed tomography and/or magnetic resonance imaging.

Another variation of a system for positioning a radiation source may comprise a circular gantry, a radiation source mounted on the gantry, positron emission detectors mounted on the gantry, and a controller in communication with the radiation source and the positron emission detectors. The positron emission detectors may be configured to detect a single positron annihilation emission path that intersects a region of interest within a coordinate system. The controller may be configured (e.g., by programming an algorithm that is stored in memory) to compute an attenuation factor of the emission path using an image of the region of interest acquired by a selected imaging modality, and to position the radiation source along the emission path. The radiation source may be configured (e.g., by a program stored in memory and/or one or more signals from the controller) to generate radiation that is modulated by the attenuation factor. The selected imaging modality may be computed tomography and/or magnetic resonance imaging. In some examples, the radiation source may be configured to generate radiation that is adjusted to compensate for attenuation of the radiation along the positron annihilation emission path. Alternatively or additionally, the radiation source may be configured to generate radiation that is proportional to the attenuation of the detected positron annihilation emission path. In other examples, the radiation source may be configured to generate radiation that is inversely proportional to the attenuation of the detected positron annihilation emission path. Alternatively or additionally, the radiation source may be configured to generate radiation having an intensity that is modulated proportionally to the attenuation factor, and/or radiation with a time duration that is modulated proportionally to the attenuation factor, and/or radiation with an intensity that is modulated inversely proportionally to the attenuation factor, and/or radiation with a frequency that is modulated inversely proportionally to the attenuation factor.

Another variation of a system for positioning a radiation source may comprise a circular gantry, a radiation source mounted on the gantry, positron emission detectors mounted on the gantry, and a controller in communication with the radiation source and the positron emission detectors. The positron emission detectors may be configured to detect a single positron annihilation emission path that intersects a first PET-avid region of interest and a second PET-avid region of interest within a coordinate system. The controller may be configured (e.g., by programming an algorithm that is stored in memory) to position the radiation source to a location along the emission path, and the radiation source may be configured (e.g., by a program stored in memory and/or one or more signals from the controller) to generate radiation that is adjusted according to a modulation factor that is inversely proportional to a projection of the first PET-avid region of interest on the location of the radiation source. In some variations, the radiation source may be configured to generate a radiation beam with a time duration that is modified by the modulation factor. Alternatively or additionally, the radiation source may be configured to generate radiation with an intensity that is modified by the modulation factor. In some examples, the second PET-avid region of interest may intersect with a third region of interest, and the first region of interest may not intersect with the third region of interest.

One variation of a system for emission guided radiation therapy may comprise a gantry movable about a patient area, a plurality of positron emission detectors arranged movably along the inner gantry configured to detect a plurality of positron annihilation emission paths within the patient area and a radiation source arranged movably along the outer gantry. The gantry may comprise a rotatable inner gantry and a rotatable outer gantry, and the radiation source may be arranged movably along the outer gantry. The radiation source may be configured to apply radiation along the plurality of positron annihilation emission paths within the patient area, and the inner gantry may be capable of rotating at a higher rate than the outer gantry. Optionally, the system may further comprise single-photon emission detectors arranged movably along the inner gantry. In some variations, the radiation source may comprise a collimator. Such a system may optionally comprise a sense mode where the plurality of positron emission detectors obstructs the radiation source, and a firing mode where the radiation source is unobstructed and is able to apply radiation to the patient area.

BRIEF DESCRIPTION OF THE DRAWINGS

FIGS. 6A to 6C are conceptual depictions of an example of an EGRT method where a plurality of radiation beams are applied along a single LOR.

FIGS. 8A and 8B are conceptual depictions of an EGRT method that updates the location information for a tumor and/or PTV during EGRT.

DETAILED DESCRIPTION

Described herein are systems and methods for positioning a radiation source with respect to one or more regions of interest in a coordinate system. In some variations, such systems and methods may be used for emission guided radiation therapy for the delivery of radiation along emission paths of photons from positron annihilation events. The systems and methods described here may be used to deliver an elevated dose of radiation to a first region of interest (e.g., tumors), while delivering little, if any, radiation to a second region of interest (e.g., peripheral tissues). The systems and methods described below may be able to precisely locate a targeted tumor region so that an elevated level of radiation may be applied to the tumor(s) while preserving the tissue around the tumor(s). These systems and methods may help to provide accurate tumor localization, and may be used to deliver radiation beams to the target tumor region in real-time (e.g., within seconds after a positron annihilation emission path has been detected). These systems and methods may handle and manage uncertainties originating from multiple processes such as tumor volume delineation, patient setup and physiologic motion in order to provide useful radiation treatment. The systems and methods described herein may help improve radiation treatment efficiency, patient comfort, and/or cost effectiveness. While the variations and examples described below refer to EGRT systems, it should be understood that these are merely examples of systems that may be used to position a radiation source with respect to one or more regions of interest in a coordinate system. Regions of interest within a coordinate system may include, but are not limited to, tumor tissue, non-tumor tissue, radiation-sensitive organs or structures, any anatomical structures, any regions or volumes that emit positrons (e.g., PET-avid regions), any regions that do not emit positrons (e.g., non-PET-avid regions), regions or volumes that may be defined with respect to a PET-avid region, stationary regions or volumes, moving regions or volumes, any region or volume identified by a user or practitioner (e.g., a planning target volume) or a machine algorithm (e.g., an image processing algorithm) and the like.

EGRT may be used alone or in conjunction with other types of radiation therapies. For example, EGRT may be used with intensity modulated radiation therapy (IMRT) and/or image guided radiation therapy (IGRT). IMRT may be capable of generating highly conformal dose distributions to deliver radiation to a targeted tumor region while sparing healthy tissues. IGRT may use imaging modalities such as MRI or CT in pre-treatment planning to locate the tumor(s) within the patient. Combining either or both of these imaging modalities with EGRT may be useful for real-time location tracking of the targeted tumor region to help ensure that the therapeutic radiation is directed to the intended tissue region.

Figure 1:
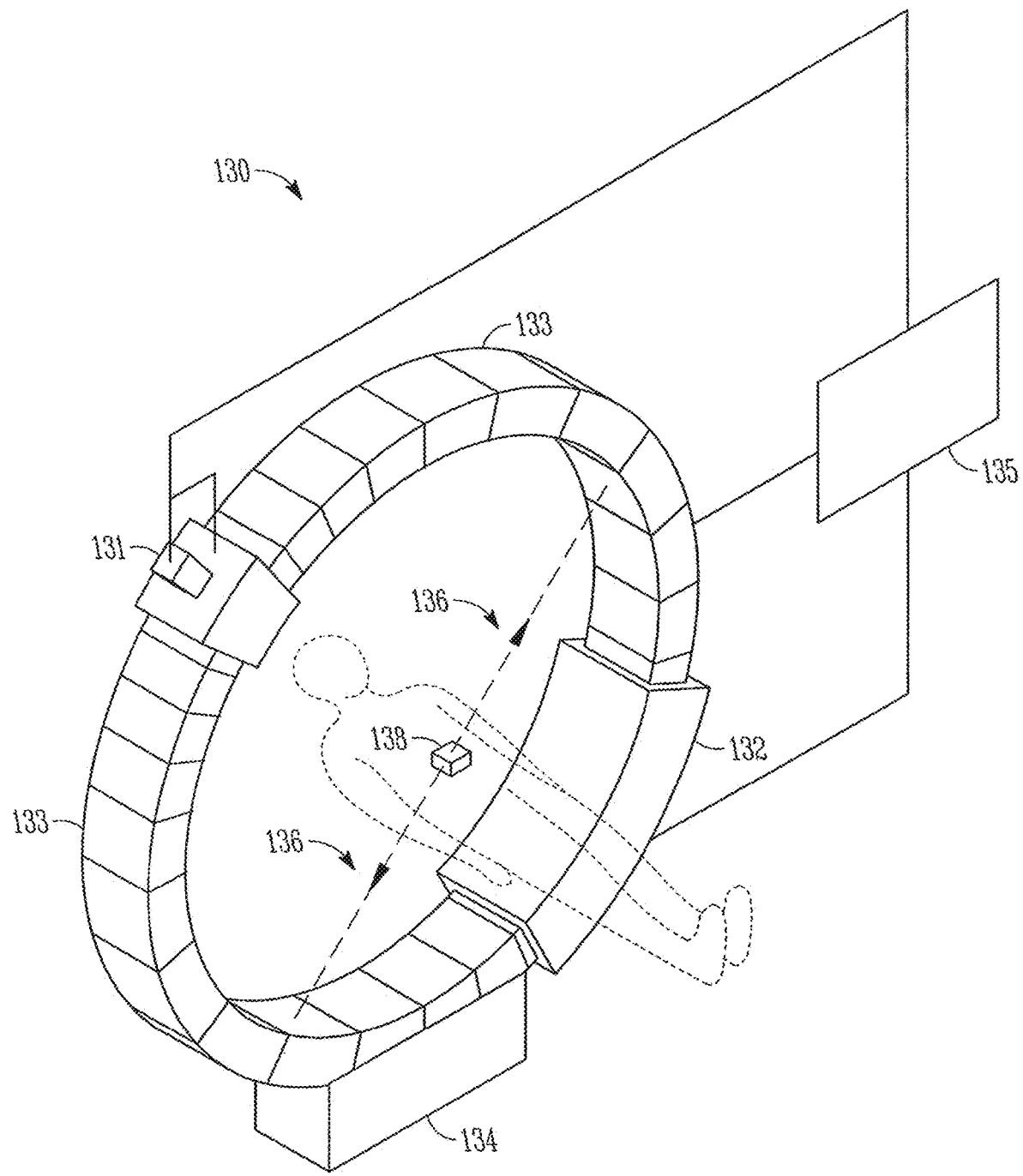
FIG. 1 is one variation of an emission guided radiation therapy system for aligning radiation along positron annihilation emission paths.

Disclosed herein are systems and methods for EGRT using a PET tracer, where radiation may be applied along a line of response (LOR) that is aligned with a detected coincident positron annihilation emission path. Systems that may be used for EGRT may comprise a gantry movable about a patient area, one or more positron emission detectors that may be movable along the gantry, and one or more therapeutic radiation sources that may also be movable along the gantry. The one or more positron emission detectors may be capable of detecting and tracking the emission paths corresponding to a plurality of regions of interest (e.g., tumors). The one or more radiation sources may be configured to compensate for the motion of each of the plurality of tumors so that radiation may be accurately applied to the tumor(s) and not to healthy tissue. One variation of a system (130) for positioning a radiation source that may be used for emission guided radiation therapy is depicted in FIG. 1. The system (130) may comprise a circular moveable gantry (not shown), a radiation source (131) mounted on the gantry, one or more positron annihilation emission sensors (133) positioned at various locations on and around the gantry, one or more x-ray detectors (132), a motion system (134), and a controller or microprocessor (135). The x-ray detectors (132) and positron annihilation emission sensors (133) may also be mounted on the moveable gantry. In some variations, the positron emission sensors (133) and the x-ray detectors (132) may be arranged around a substantial portion of the perimeter of the gantry. The positron emission sensors (133) may be configured to detect positron annihilation events by sensing the emission paths (136) of the photons resulting from the annihilation events. The motion system (134) may be configured to move the gantry and attached equipment about a region of interest or target volume (138) to align the radiation source (131) with the detected emission path (136). The microprocessor (135) may be connected to the radiation source (131), positron emission sensors (133), x-ray detectors (132) and the motion system (134) in order to regulate the motion of each of these components with respect to each other, as well as to activate each of these components in a desired sequence. For example, the microprocessor (135) may identify the coincident photon emission path (136) that intersects the target volume (138), and may coordinate the alignment, configuration, and triggering of the radiation source (131) to direct radiation to the target volume (138) along the detected emission path (136).

The microprocessor (135) may control the rotation of the gantry to adjust the position of the radiation source (131) in response to a plurality of detected emission paths in the course of an EGRT session. The microprocessor of an EGRT system may comprise a computer readable storage medium and may be able to execute various functions in accordance with software or firmware stored in the computer readable storage medium. Examples of computer readable storage mediums can include, but are not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like. The software or firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. Examples of transport mediums can include, but are not limited to, an electronic, magnetic, optical, electromagnetic or infrared wired or wireless propagation medium.

While the systems and methods for EGRT described herein may be configured to detect and respond to emission paths from coincident positron annihilation emission events arising from PET tracers, other types of radioactive tracers may also be used for EGRT. For example, EGRT systems and methods may additionally or alternatively be configured to detect and respond to single photon emissions arising from SPECT tracers. Other radioactive tracers that are commonly used in nuclear medicine may also be used with the EGRT systems and methods described herein. Emission rays from such radioactive tracers may serve as guidance for accurate and near real-time tumor tracking. Depending the on type of radioactive tracer that is used, EGRT systems may comprise a variety of detectors, such as positron emission detectors, single-photon emission detectors, and the like. EGRT systems may also comprise a variety of therapeutic radiation sources, including linear accelerators, radioactive materials, x-ray sources, particle beam sources, etc. In some variations, a radiation source may comprise a collimator capable of delivering radiation in response to single photon events. One example of a system that may be used for EGRT is described in U.S. Pat. No. 7,265,356 filed on Nov. 29, 2004. Additional descriptions and examples of EGRT systems are provided below, as well as in U.S. Pat. Appl. Publ. No. 2009/0256078 filed on Feb. 9, 2009, which is hereby incorporated by reference in its entirety.

Methods for EGRT may be used to track the location of tumors in real time, and/or may be used to deliver a desired dose of radiation to tumor(s) in a planning target volume (PTV) while sparing peripheral tissue. A PTV may be determined during a pre-treatment and/or planning session by a physician and/or technician (e.g., radiation oncologist, medical physicist, radiologist, radiation therapist, etc.) using a variety of imaging modalities, such as CT, PET, MRI, x-ray, etc., either alone or in combination. A PTV may also be determined during a radiation therapy session. For example, a PTV may be determined periodically during a radiation therapy session using one or more types of on-board imaging modalities (e.g., CT, PET, MRI, X-ray, etc.), either alone or in combination. Data pertaining to a PTV may be stored in the microprocessor of an EGRT system for use by a medical physicist and/or radiation therapist during the radiation therapy session. A PTV may include the tumor region and peripheral non-tumor tissue in the region of the tumor region, or a PTV may include only the tumor region without the peripheral non-tumor tissue. Alternatively or additionally, a PTV may include the visible location and growth of a tumor as determined by a selected imaging modality (e.g., CT, PET, MRI, X-ray, SPECT, etc). In some cases, a PTV may include a PET-avid tissue region (i.e., a tissue volume that has taken up PET tracer and is emitting photons resulting from positron annihilations), and in other cases, a PTV may include both the PET-avid region and adjacent non-PET-avid tissue regions. In some variations, a PTV may include the regions described above with one or more additional margins, for example, margins for patient and/or organ motion, organ shape and size variation, and uncertainties in radiation beam alignment.

Some methods may help to compensate for tumor and/or PTV movement due to respiration or other patient movement, and/or provide for more accurate or precise tumor edge detection, and/or help to ensure that the radiation applied to a PTV is homogeneous by reducing "hot" or "cold" spots in the PTV (e.g., such that the radiation dose is uniformly delivered across the entire PTV). While various methods for EGRT are individually described below, it should be understood that one or more of the methods disclosed herein may be combined before or during an EGRT session. Optionally, one or more of these methods of EGRT may be used in conjunction with surgery, chemotherapy, brachytherapy, and/or other cancer therapies in the course of the cancer treatment of a patient.

Figure 1A:
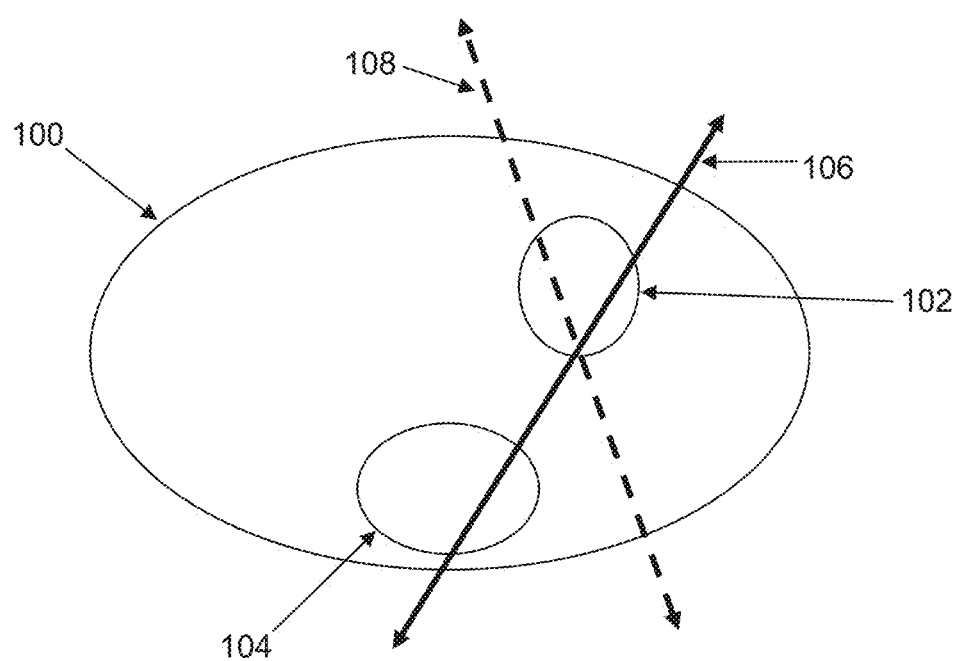
FIG. 1A is a conceptual depiction of an example of an EGRT method for probabilistically applying radiation along a line of response (LOR) that intersects both a planning target volume (PTV) and a radiation-sensitive structure.

One variation of a method for EGRT may deliver a reduced quantity of radiation to radiation-sensitive structures while delivering a prescribed dose of radiation to a tumor located in a PTV. Certain variations of such methods may avoid delivering any radiation to a selected tissue region or any radiation-sensitive structures. A radiation-sensitive structure may be, for example, an organ that is particularly prone to radiation damage. Radiation-sensitive structures may include the heart, esophagus, rectum, stomach, upper and lower intestines, breast, salivary glands organs involved in gametogenesis, the spinal cord and other neural tissue, etc. In some variations of EGRT, radiation-sensitive structures may optionally be treated with a radio-protector (e.g., amifostine), which may help these radiation-sensitive structures self-repair any radiation damage. One variation of a method that delivers a reduced quantity of radiation to radiation-sensitive structures may comprise delivering radiation less frequently along coincident positron annihilation emission paths or LOR that intersect with the radiation-sensitive structures. FIG. 1A conceptually depicts a patient area (100) with a planning target volume PTV (102) and a radiation-sensitive structure (104). At least a portion of the PTV (102) has taken up a PET tracer (e.g., FDG, FLT, F-MISO), and may be emitting photons resulting from positron annihilation events, i.e., at least a portion of the PTV may be PET-avid. An emission path or line of response originating within the PTV may intersect the radiation-sensitive structure (104), such as line of response (106), while others may not intersect the radiation-sensitive structure (104), such as line of response (108). A radiation source (not shown) may apply radiation along the LOR (108) at a certain frequency and intensity to deliver a prescribed dose to the PTV (102). The radiation source may apply radiation that has been attenuated or modulated (e.g., in frequency and/or intensity) along the LOR (106) to reduce the radiation exposure to the radiation-sensitive structure (104). For example, the frequency with which radiation is delivered along the LOR (106) may be reduced in a probabilistic manner. Alternatively or additionally, radiation delivered along the LOR (106) may be attenuated (e.g., reduced intensity or power) as compared to the radiation delivered along the LOR (108).

Figure 1B:
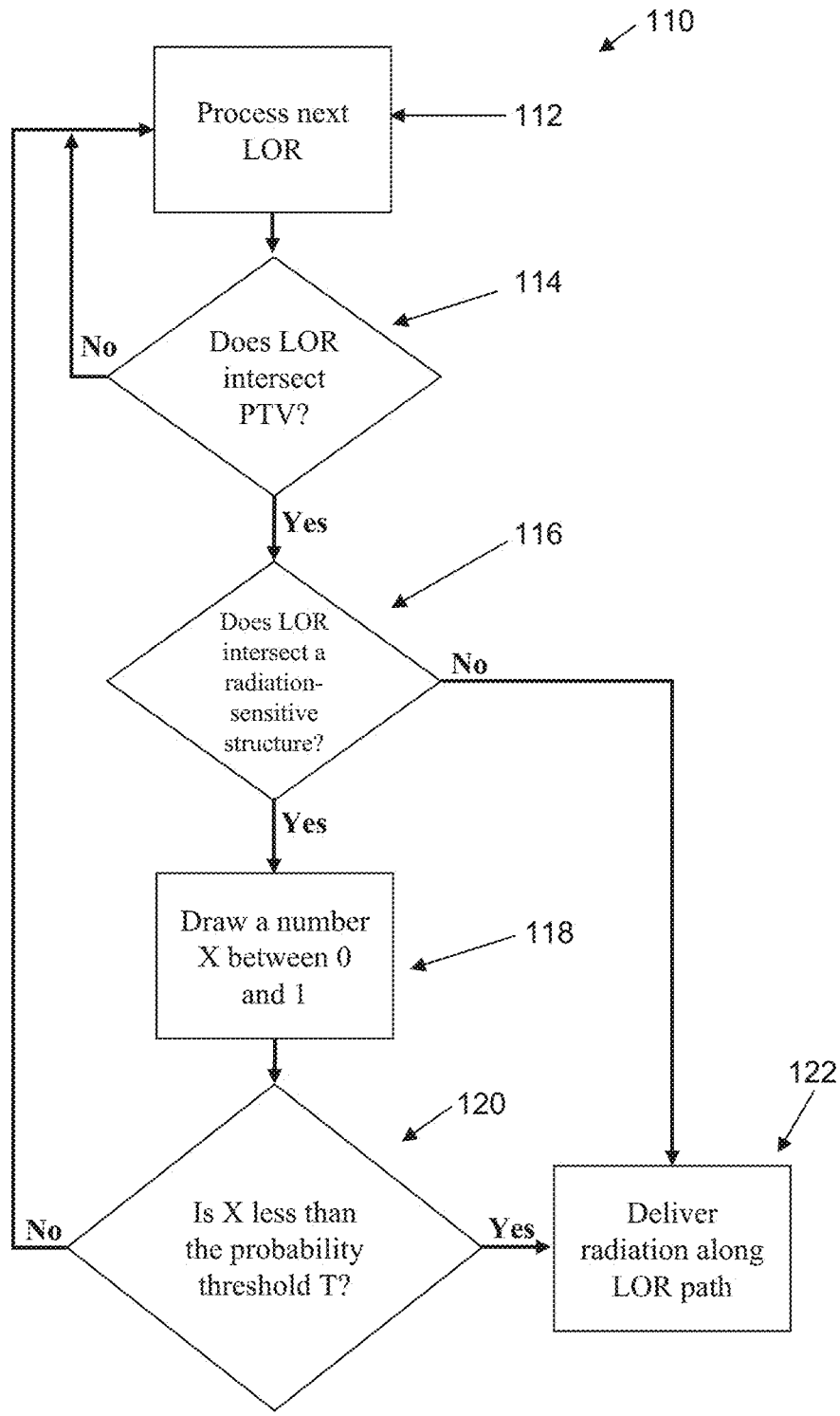
FIG. 1B is a flowchart diagram of one example of an EGRT method that functions according to the depiction in FIG. 1A.

One example of a method (110) of delivering a reduced quantity of radiation to radiation-sensitive structures while delivering a prescribed dose of radiation to a PTV is diagrammatically represented in FIG. 1B. The method (110)

may, for example, reduce the frequency with which radiation is applied along a LOR that intersects a radiation-sensitive structure. This method may be implemented using an EGRT system comprising a movable gantry, one or more positron emission detectors along the gantry, one or more radiation sources mounted on the gantry, a motion system, and a microprocessor. Processing a LOR (112) may comprise detecting a single coincident positron annihilation emission path using a positron emission detector, and may optionally comprise storing data (e.g., location data, signal strength data, etc.) about the LOR in a memory of the microprocessor. Next, the microprocessor may evaluate whether the LOR intersects a PTV (114) by comparing the location data of the LOR with location data of the PTV stored in the memory of the microprocessor. If not, the EGRT system may return to the initial state (112) to detect another LOR. If so, the microprocessor may evaluate whether the LOR intersects a radiation-sensitive structure (116) by comparing the location data of the LOR with location data of the radiation-sensitive structure. If not, the microprocessor may send an instruction to a radiation source of the EGRT system to apply radiation along the LOR (122). If so, the microprocessor may randomly generate a number X between 0 and 1 (118). The microprocessor then determines whether the number X is below a pre-programmed probability threshold T (120). If not, then the EGRT system may return to the initial state (112) to detect another LOR. If the modulation number X is below a pre-programmed threshold T, then the microprocessor may send an instruction to the radiation source to apply radiation along the LOR (122). Once radiation has been delivered along the detected LOR, the method (110) may be repeated as may be desirable, e.g., until a prescribed dose of radiation has been applied to the PTV and/or the radiation-sensitive structure. As an example, it may be desirable to prescribe dose to a radiation-sensitive structure that is no more than 20% of the dose level of the surrounding tissue and/or PTV. In this example, the probability threshold T may be selected to be 0.2, so that radiation is delivered to one out of every five lines of response that intersect both the radiation-sensitive structure and the PTV. Alternatively, the probability threshold T may also represent an attenuation or scale factor by which the radiation is modulated. For example, the radiation that is applied along a LOR that intersects both a PTV and a radiation-sensitive structure may be modulated by the probability threshold of T=0.2 such that the radiation applied is at 20% of the nominal intensity level. Alternatively, the nominal leaf-open time of the radiation source may be 20% of the nominal leaf-open time. The probability threshold T may be any suitable value, for example, 0, 0.005, 0.01, 0.05, 0.10, 0.5, 0.75, 0.9, 1.0 etc. In other variations, the intensity or power of the radiation applied along a LOR may be attenuated or scaled by a probabilistic coefficient. A probabilistic coefficient may be derived from a randomly generated number between 0 and 1 that is less than the threshold T.

Figure 1C:
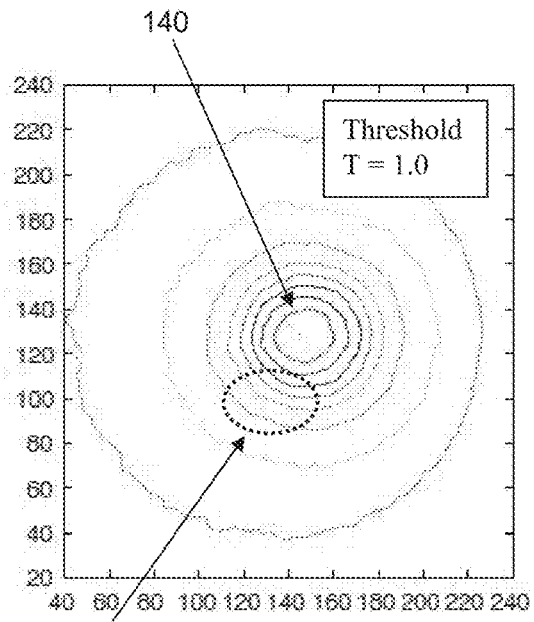
FIGS. 1C to 1E depict contour plots (with uniform contour intervals) derived from computer simulations using the method of FIG. 1B.
Figure 1D:
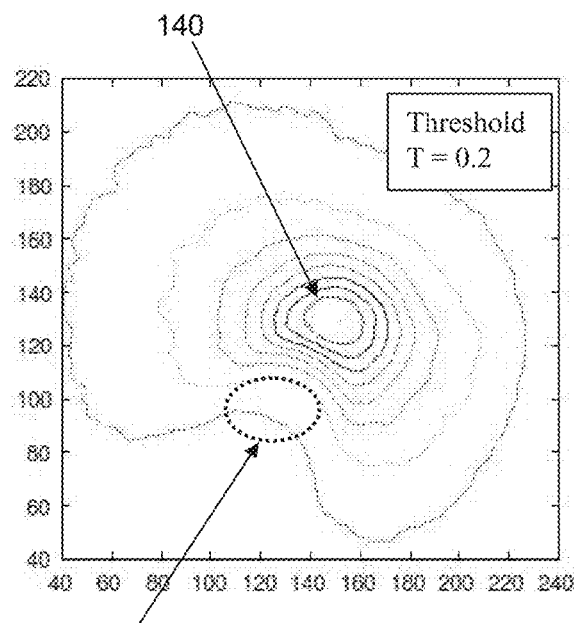
Figure 1E:
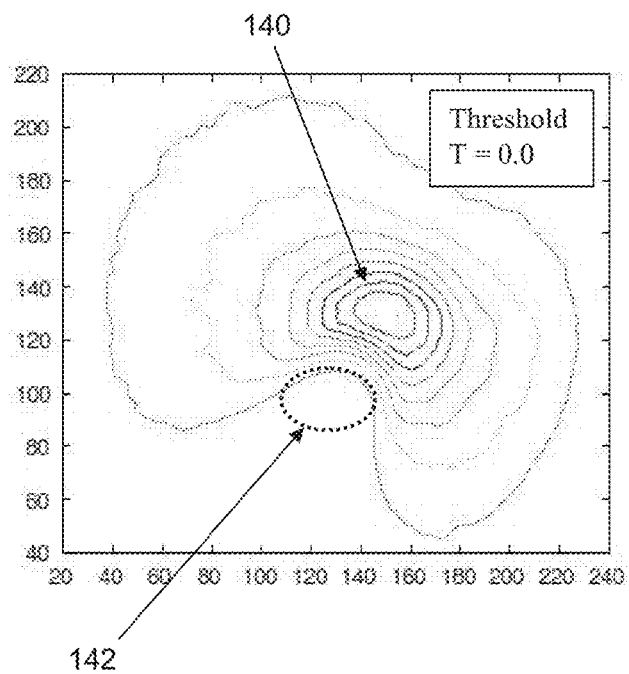

FIGS. 1C to 1E are contour plots that represent computer-simulated radiation dose maps when the method (110) is implemented to apply radiation to a PTV (140). The different contour plots in FIGS. 1C to 1E have uniform contour intervals and reflect the effect of varying the probability threshold T on the amount of radiation applied to a radiation-sensitive structure (142). FIG. 1C depicts the dose profile when the probability threshold T=1.0 (i.e. no penalty to delivering dose to the radiation-sensitive structure). In this example, the radiation dose to the radiation-sensitive structure (142) is similar to the radiation dose of surrounding tissue. FIG. 1D depicts the dose profile when the probability threshold T=0.2, and FIG. 1E depicts the dose profile when the probability threshold T=0.0. As the probability threshold T decreases towards zero, the total dose to the radiation-sensitive structure (142) may decrease as depicted in the contour maps.

Figure 2A:
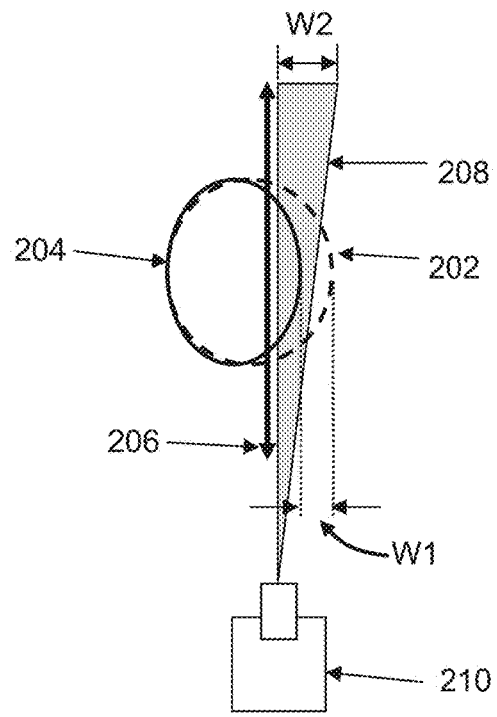
FIG. 2A is a conceptual depiction of another variation of an EGRT method for applying a radiation beam with a width that corresponds to a width of a substantially perpendicular extension region of the PTV.

In other variations of EGRT methods, the radiation source may adjust the properties of the radiation beam delivered to the PTV to deliver radiation to non-PET-avid tissue within the PTV. For example, the width of the radiation beam may be expanded to deliver radiation to non-PET-avid tissue within the PTV, and/or multiple radiation beams may be applied over time at non-PET-avid locations within the PTV. One example of such a method is conceptually depicted in FIG. 2A. This method may comprise acquiring images (e.g., one or more of CT, MRI, PET, etc., including PET-CT images) during a treatment planning phase to define the planning target volume or volumes to be treated during EGRT. The margin extended PTV (202) may extend with a width (W1) from the edge of the PET-avid target volume (204). During an EGRT session, when a LOR (206) that intersects the PTV (202) is detected by a positron emission detector (not shown), a radiation beam (208) applied by the radiation source (210) may be adjusted so that the radiation beam width (W2) is wider in the direction of added margin between the PET-avid volume (204) and PTV (202). In some variations, the width (W2) of the radiation beam may be extended in the direction of the margin if the radiation beam (208) is substantially perpendicular to the margin extension direction.

Figure 2B:
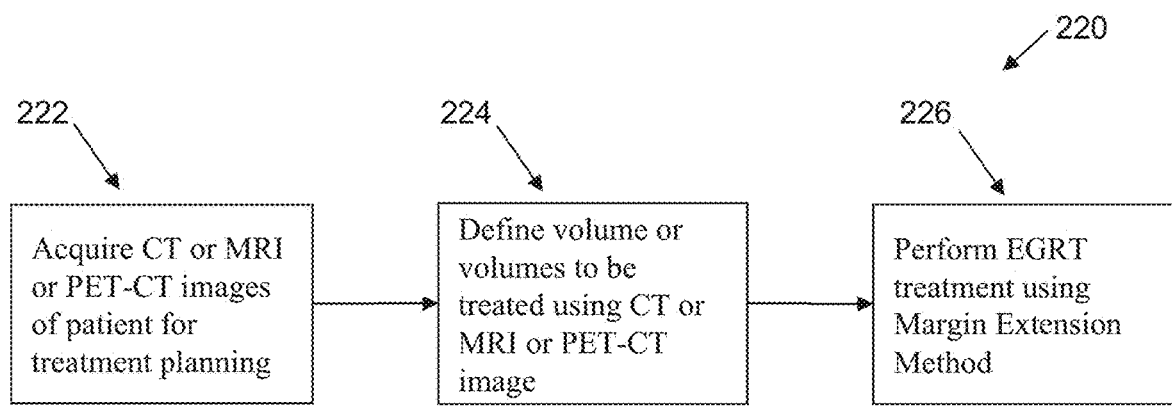
FIG. 2B is a flowchart diagram of one method that may be used to define an extension region of the PTV.
Figure 2C:
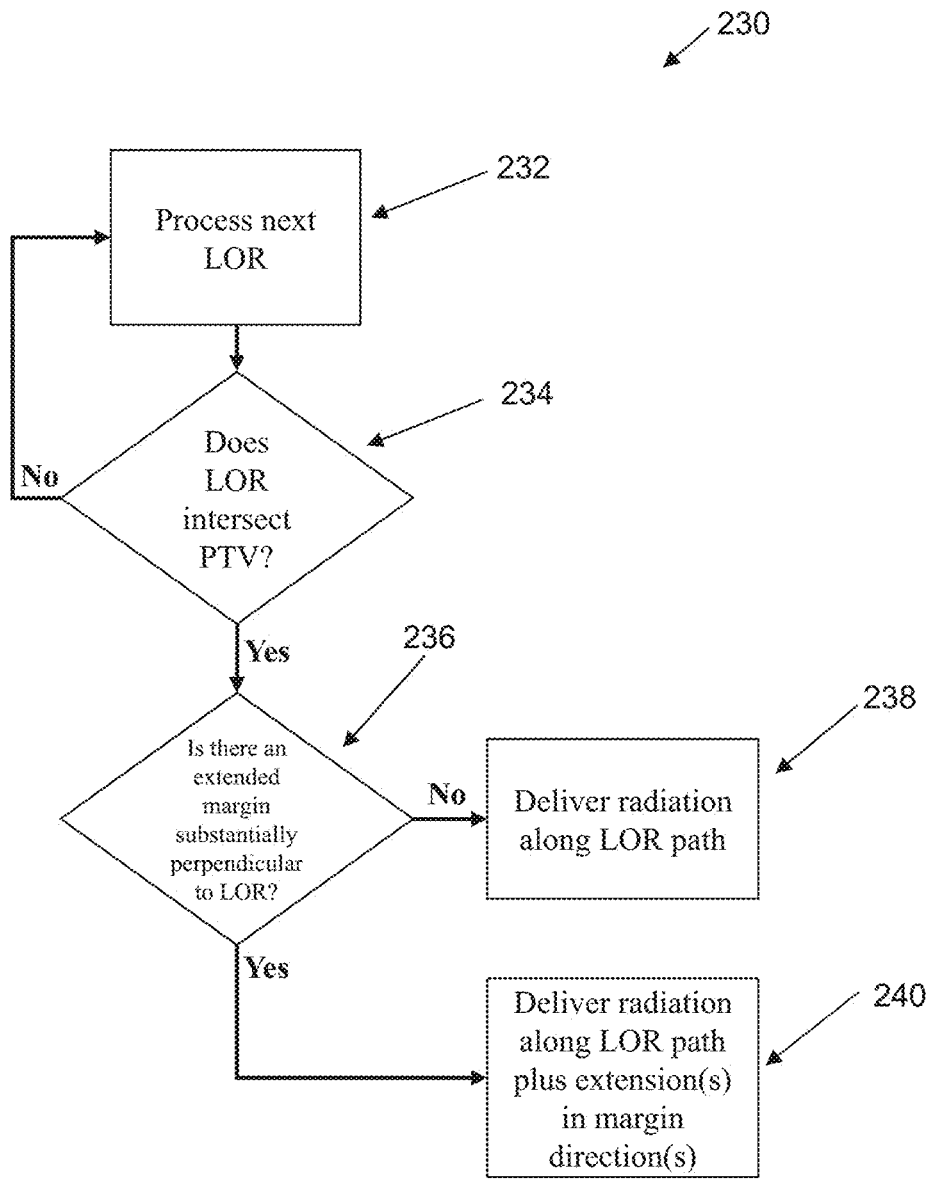
FIG. 2C is a flowchart diagram of an exemplary implementation of the method depicted in FIG. 2A.

One example of a method that applies radiation to tissue adjacent to the boundaries of a PET-avid volume within a PTV is depicted in FIGS. 2B and 2C. FIG. 2B depicts a method (220) that may be used during treatment planning, which may take place prior to the EGRT session, or may take place during the EGRT session. The method (220) may comprise acquiring (222) one or more images, such as CT, MRI, PET and/or composite PET-CT images. Based on the image(s) acquired, the PTV(s) may be defined (224) by locating a PET-avid region. Optionally, any extension margins beyond the PET-avid volume(s) may also be defined, e.g., PTV(s) may comprise a PET-avid tissue and non-PET-avid tissue adjacent to the PET-avid tissue. In some variations, the treatment volume(s) and/or extension margins beyond the PET-avid volume may be defined by additional patient data, computer-executed image processing algorithms, and/or practitioner input, and may have a length and or width beyond the edge of the PET-avid volume(s). Information about the PET-avid volume and/or extension margins (e.g., the length, width, volume, orientation of the margin extension with respect to the target volume, etc.) that define a border of a PTV may be stored in a memory of a microprocessor of an EGRT system for use during the treatment session.

FIG. 2C depicts one example of an EGRT method (230) that may use the information from the method (220) to provide radiation treatment to a patient. This method may be implemented using an EGRT system as described above and further described below. The imaged PET-avid volume, and margin extension data (e.g., the length, width, volume, orientation of the margin extension with respect to the target volume, etc.) from the method (220) may be stored in a memory of a microprocessor of the EGRT system prior to the EGRT session. Alternatively or additionally, extension margins may be determined or computed by the EGRT system at any point during the session by acquiring one or more images during treatment, such as CT, MRI, PET and/or composite PET-CT images. Processing a LOR (232) may comprise detecting a single coincident positron annihilation emission path using a positron emission detector, and may optionally comprise storing data about the LOR (e.g., location data, signal strength data, etc.) in a memory of the microprocessor. Next, the microprocessor may evaluate whether the LOR intersects a PTV (234) by comparing the location data of the LOR and location data of the PTV. If not, the EGRT system may return to the initial state (232) to detect another LOR. If so, the microprocessor may use the data from the method (220) to compute (236) whether the LOR is substantially perpendicular to the margin extension direction. If not, the microprocessor may send an instruction to a radiation source of the EGRT system to apply radiation along the LOR (268). If the LOR is computed to be substantially perpendicular to the margin extension direction, the microprocessor may send an instruction to the radiation source to deliver (240) a radiation beam along the LOR, where the radiation beam has a width that corresponds to a width of the extension margin. In some variations, the extension margin may be computed by a microprocessor of the EGRT system during the session and may be used alone or in conjunction with any extension margins that may have been determined during a treatment planning phase. Once radiation has been delivered along the LOR, the method (230) may be repeated as may be desirable, e.g., until a prescribed dose of radiation has been applied to the PTV.

Figure 3A:
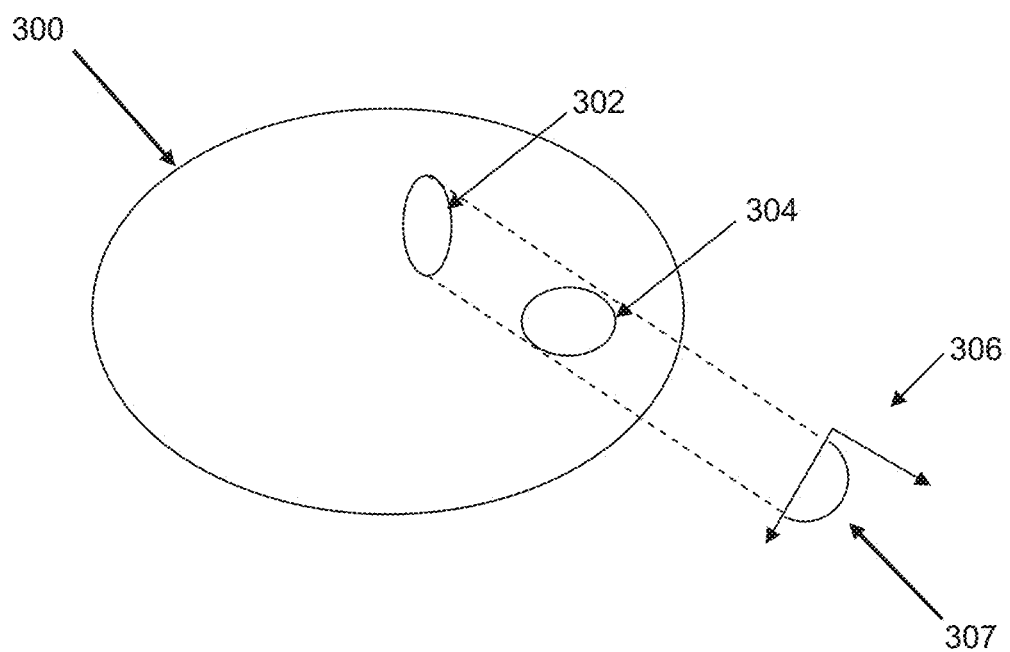
FIG. 3A is a conceptual depiction of another EGRT method for applying a radiation beam that distinguishes between PET-avid regions within a PTV and PET-avid regions outside of a PTV.

Some variations of EGRT methods may distinguish between coincident positron annihilation emission paths that originate from a planning target volume and emission paths that originate outside of the planning target volume. Positron annihilation events may take place outside of a PTV, and increased uptake of certain PET-tracers such as FDG may occur, for instance, in the heart, brain, areas of inflammation, infected areas of the lung, or other anatomical regions. For example, the PET tracer may be taken up by tissues in a plurality of locations, and EGRT may be planned for only a subset of those locations (i.e., some PET-avid tissues may be suitable targets for radiation while other PET-avid tissues may not). FIG. 3A depicts a patient area (300) that has a first PET-avid volume (302) and a second PET-avid volume (304). In this example, the first PET-avid volume (302) may not be part of a PTV. The second PET-avid volume (304) may be located within a PTV. An EGRT method that does not distinguish between coincident positron annihilation emission paths that originate from within a PTV and emission paths that originate outside of the PTV may apply an increased radiation dose in the directions connecting the PTV with the PET-avid regions outside of the PTV. One way in which an EGRT method may avoid creating localized regions of relatively higher radiation may comprise computing a mathematical projection of PET-avid volumes outside of the PTV for each position that a therapeutic radiation source may occupy. For example, the first PET-avid volume (302) may have a projection (306) for a radiation source at location (307). Similar projections of PET-avid volumes outside of a PTV may be computed for one or more of the radiation source locations on a gantry of an EGRT system. In some variations, the computed projections may be used to modulate the time or intensity or number of firings of the radiation delivered along each path that is inversely proportional to the value of the projection at a particular location. For example, a PET-avid region outside of the PTV may result in a higher relative projection value along a path through the PTV as compared to a different path through the PTV. The radiation source may deliver radiation in accordance with a computed projection value. For example, an increased projection value at a certain location of the gantry may signal the therapeutic radiation source to deliver proportionally less radiation from that location than a reduced projection value would. The radiation delivered may be modulated in various ways, for example, in time, intensity, or number of firings along the emission path.

Figure 3B:
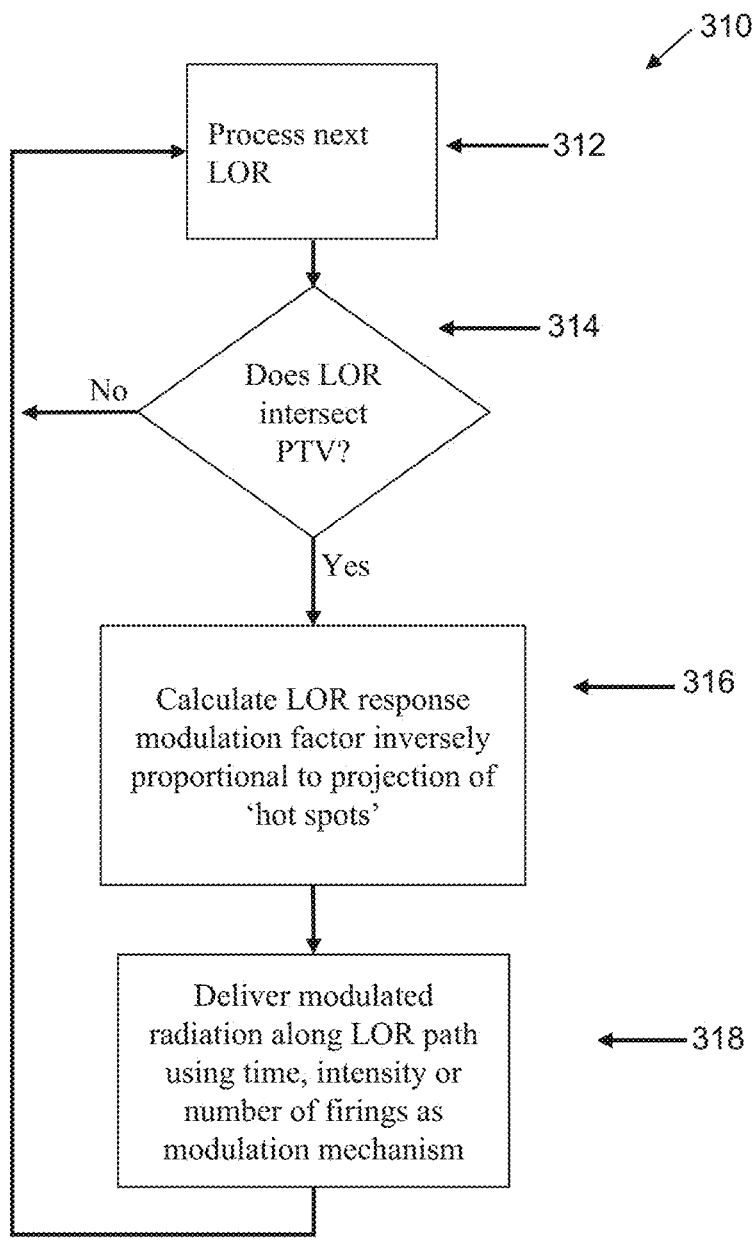
FIG. 3B is a flowchart diagram of an exemplary implementation of the method depicted in FIG. 3A.

One example of a method (310) of avoiding the creation of localized regions of high radiation is diagrammatically represented in FIG. 3B. The method (310) modulates the radiation that is applied along a LOR according to the projection of a "hot spot" at the location of the radiation source. This method may be implemented using an EGRT system comprising a movable gantry, one or more positron emission detectors along the gantry, one or more radiation sources along the gantry, a motion system, and a microprocessor. Processing a LOR (312) may comprise detecting a single coincident positron annihilation emission path using a positron emission detector, and may optionally comprise storing data about the LOR (e.g., location data, signal strength data, etc.) in a memory of the microprocessor. Next, the microprocessor may evaluate whether the LOR intersects a PTV (314) by comparing the location data of the LOR with location data of the PTV that may be stored in the microprocessor memory. If not, the EGRT system may return to the initial state (312) to detect another LOR. If so, the microprocessor may compute a modulation factor that is inversely proportional to the projection of one or more PET-avid regions that are not in the PTV (316). The computed modulation factor may be used to adjust the frequency, duty cycle, intensity, number of firings, and/or other characteristics of the radiation beam. The microprocessor may then provide an instruction to the radiation source to modulate the radiation beam according to the modulation factor. The radiation source may then deliver (318) the modulated radiation along the LOR. Once radiation has been delivered along the detected LOR, the method (310) may be repeated as may be desirable, e.g., until a prescribed dose of radiation has been applied to the PTV.

Figure 4A:
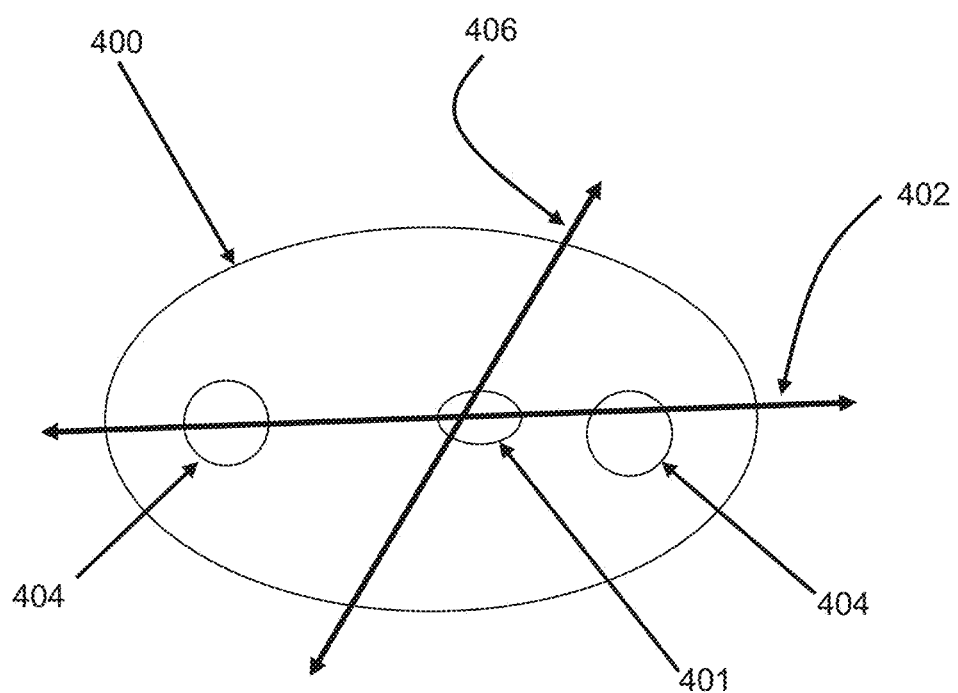
FIG. 4A is a conceptual depiction of another EGRT method for applying a radiation beam that corrects for attenuation along a coincident positron emission path.

Some methods for EGRT may compensate for any attenuation of LOR signal strength that may occur due to density variations within the subject. FIG. 4A conceptually depicts a patient area (400) with a PET-avid volume (401) and areas of higher density. Areas of increased density may be due to the presence of prosthetic implants, organs with higher tissue density, such as bones (404), and the like. For example, a LOR (402) that intersects the bone structures (404) may be more attenuated than a LOR (406) that does not intersect any bones or areas of increased density. Various imaging modalities may be used to approximate the attenuation of the signal strength of a LOR. In some variations of EGRT, kilovoltage CT images may be used to estimate and compensate for the attenuation of the LOR signals. The LOR attenuation may also be computed based on other imaging modalities, such as cone-beam CT, MRI, X-ray, etc. Estimation of the attenuation of LOR signals may be performed in a planning phase or pre-treatment session or during the radiotherapy treatment session. In some variations, the attenuation of the LOR signals may be dynamically computed during the radiotherapy treatment session using PET or x-ray imaging techniques. The radiation beam may then be adjusted according to the attenuation of the LOR signals to compensate for LOR signal attenuation so that the correct amount of radiation is delivered to the PTV while limiting radiation to healthy tissue. In some cases, it may be desirable to apply an increased level of radiation along an attenuated LOR to compensate for the attenuation effect and to help ensure that the PTV receives a therapeutically effective level of radiation. In other cases, where the area of higher density that attenuates the LOR is a radiation-sensitive structure, it may be desirable to apply a reduced level of radiation along that LOR to reduce or limit the radiation delivered to the higher density region. For instance, a bone structure may attenuate a LOR signal, and the radiation applied along the attenuated LOR may be reduced to limit the radiation delivered to the bone structure. The radiation beam may be modulated by, for example, increasing or decreasing in magnitude or frequency to compensate for the attenuation of magnitude or frequency of the detected LOR signal. Alternatively or additionally, the radiation beam may be modulated in time (e.g., duty cycle) and/or intensity. This modulation may be implemented by calculating the density projection of a LOR along its total path through the patient, converting that projection estimate to LOR photon energies (i.e. 511 keV), and adjusting the time or intensity of the radiation response so that the amount of radiation delivered compensates for the total attenuation along the LOR path.

Figure 4B:
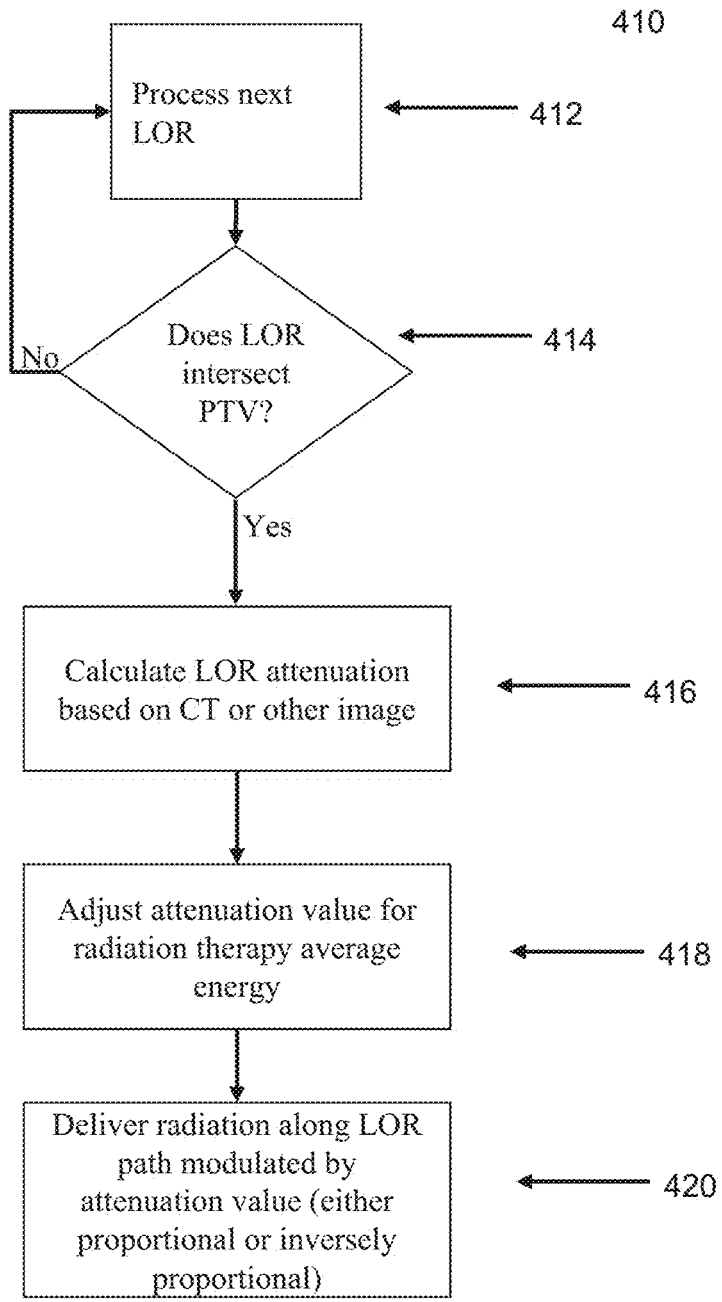
FIG. 4B is a flowchart diagram of an exemplary implementation of the method depicted in 4A.

One example of a method (410) of correcting or compensating for LOR signal attenuation so that a sufficient quantity of radiation is applied to the PTV is diagrammatically represented in FIG. 4B. The method (410) modulates the radiation that is applied along a LOR that compensates for the attenuation measured in the LOR signal. This method may be implemented using an EGRT system comprising a movable gantry, one or more positron emission detectors along the gantry, one or more radiation sources along the gantry, a motion system, and a microprocessor. Processing a LOR (412) may comprise detecting a single coincident positron annihilation emission path using a positron emission detector, and may optionally comprise storing data about the LOR (e.g., location data, signal strength data, etc.) in a memory of the microprocessor. Next, the microprocessor may evaluate whether the LOR intersects a PTV (414) by comparing the location data of the LOR with location data of the PTV that may be stored in the microprocessor memory. If not, the EGRT system may return to the initial state (412) to detect another LOR. If so, the microprocessor may compute (416) the LOR attenuation based on a kilovoltage or megavoltage CT image that may be previously entered and/or stored in a memory of the microprocessor. The attenduation of the LOR signal may be used to compute an attenuation value (418) that may be used to modulate the radiation beam. In some variations, the computed attenuation value may adjust the radiation therapy average energy by decreasing or increasing the radiation amount proportionally to the amount of LOR signal attenuation so that the correct amount of radiation is delivered along the attenuated LOR. The microprocessor may then provide an instruction to the radiation source to modulate the radiation beam according to the computed attenuation value. For example, the radiation beam may be modulated proportionally or inversely proportionally to the attenuation factor. The radiation source may then deliver (420) the modulated radiation along the LOR. Once radiation has been delivered along the detected LOR, the method (410) may be repeated as may be desirable, e.g., until a prescribed dose of radiation has been applied to the PTV.

Figure 14A:
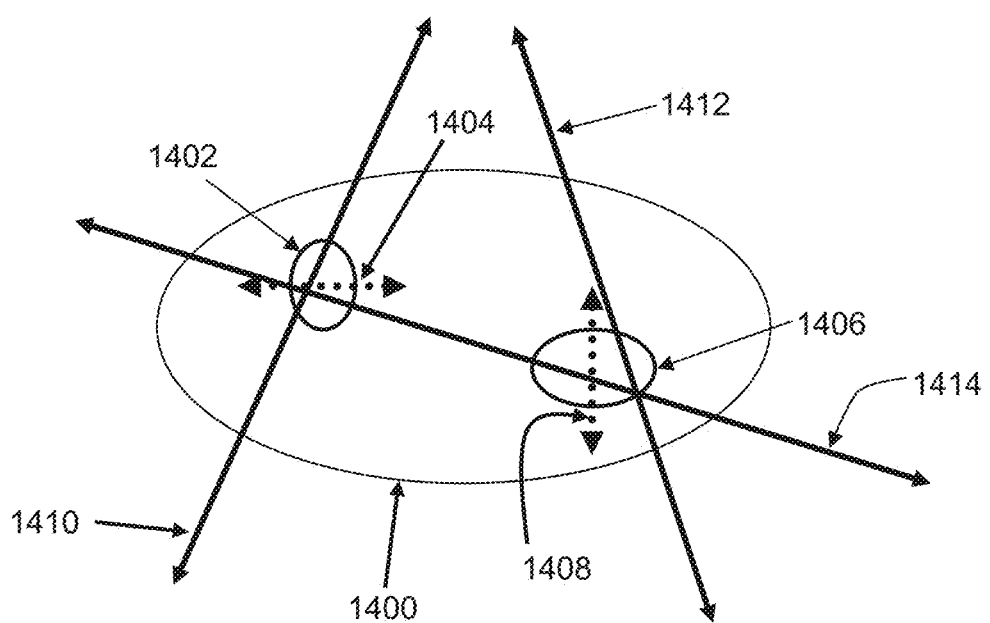
FIG. 14A is a conceptual depiction of an example of an EGRT method for applying radiation along a LOR that intersects a plurality of PTV.

One variation of a method that may be used with an EGRT system may be used for delivering radiation to a plurality of planning target volumes. The method may comprise detecting positron emission activity from multiple planning target volumes, and then applying one or more radiation beams along each detected LOR that intersects at least one of the planning target volumes. The EGRT system and this method may be able to compensate for any movement of each of the planning target volumes, regardless of the correlation of their movement, by responding to the LOR in near real-time (e.g., within seconds after a LOR has been detected). For example, a radiation beam may be applied along a detected LOR in less than 5 s, 4 s, 3 s, 2 s, 1 s, or 0.5 s, after the LOR has been detected. FIG. 14A depicts one example where a patient area (1400) has a first PET-avid region (1402) moving along arrow (1404) within a first PTV and a second PET-avid region (1406) moving along arrow (1408) within a second PTV. The movement of the first and second PET-avid volumes may be correlated or uncorrelated, LOR (1410), (1412) and (1414) represent LOR that intersect at least one of the planning target volumes. An EGRT system may apply one or more radiation beams along LOR (1410) to the first PET-avid region (1402), and/or apply radiation beams along LOR (1412) to the second PET-avid region (1406), and/or apply radiation beams along the LOR (1414) to both the first and second PET-avid regions to deliver a prescribed dose of radiation to the first and second PET-avid regions.

Figure 14B:
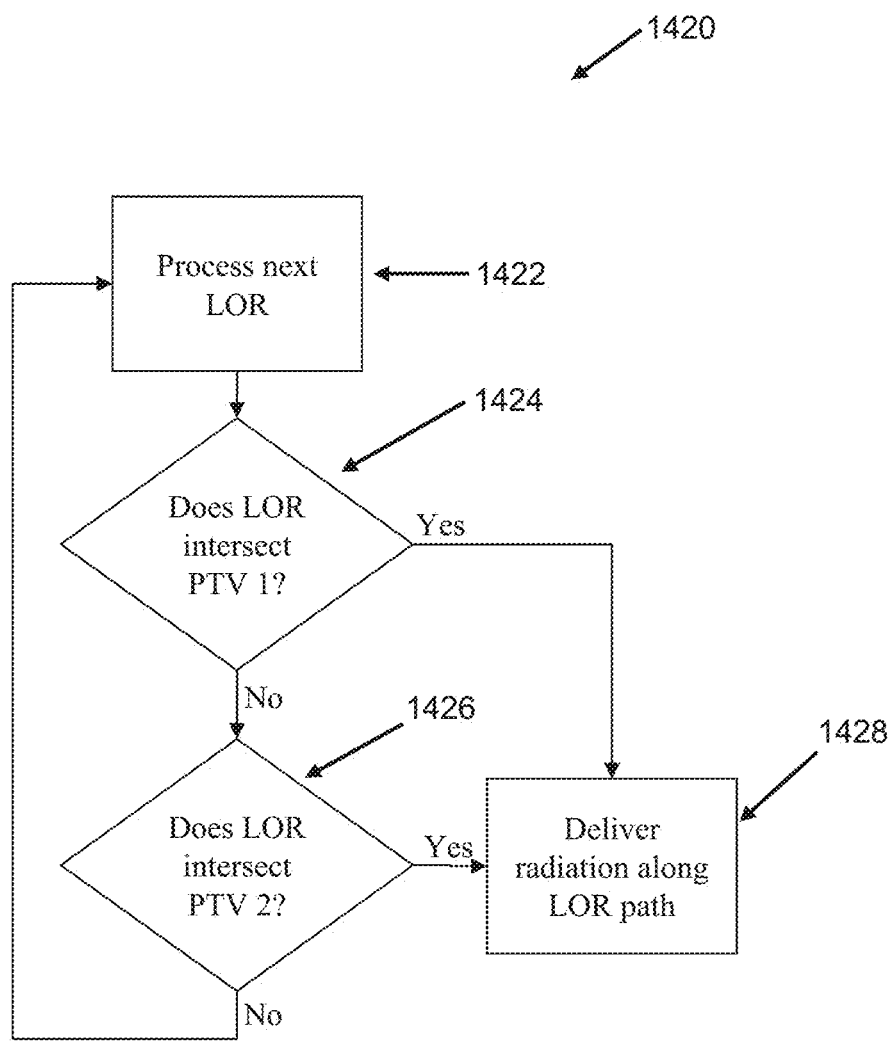
FIG. 14B is a flowchart diagram of an exemplary implementation of the method depicted in FIG. 14A.

One example of a method (1420) for delivering radiation to a plurality of planning target volumes is diagrammatically represented in FIG. 14B. This method may be implemented using an EGRT system comprising a movable gantry, one or more positron emission detectors along the gantry, one or more radiation sources along the gantry, a motion system, and a microprocessor. Processing a LOR (1422) may comprise detecting a single coincident positron annihilation emission path using a positron emission detector, and may optionally comprise storing data about the LOR (e.g., location data, signal strength data, etc.) in a memory of the microprocessor. Next, the microprocessor may evaluate whether the LOR intersects a first PTV (1424) by comparing the location data of the LOR with location data of the first PTV. If so, then the microprocessor may send an instruction to the radiation source to apply radiation along the LOR (1428). If the LOR does not intersect a first PTV, the microprocessor may evaluate whether the LOR intersects a second PTV (1426) by comparing the location data of the LOR with location data of the second PTV. If so, then the microprocessor may send an instruction to the radiation source to apply radiation along the LOR (1428). If not, then the EGRT system may return to the initial state (1422) to detect another LOR. Once radiation has been delivered along the detected LOR, the method (1420) may be repeated as may be desirable, e.g., until a prescribed dose of radiation has been applied to the first and/or second planning target volumes.

Figure 5A:
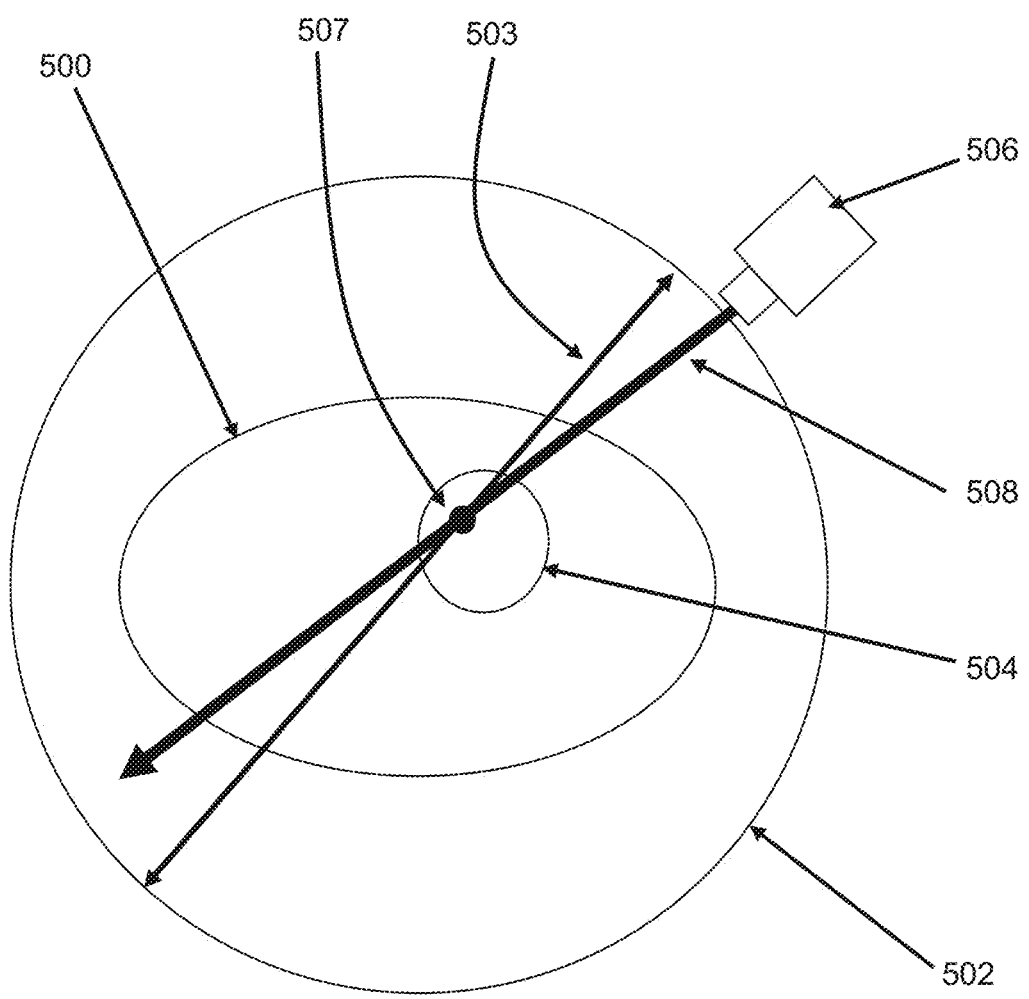
FIG. 5A is a conceptual depiction of another EGRT method for precisely applying a radiation beam along a coincident positron emission path.

Some variations of EGRT methods may be used to help the therapeutic radiation source to precisely direct radiation beams towards the PTV. One example of such a method is conceptually depicted in FIG. 5A, where a patient represented by patient area (500) is located within a central portion of a gantry (502) of an EGRT system. An LOR (503) that is detected by a positron emission detector may first be evaluated to determine whether the LOR (503) intersects with a PTV (504). In some circumstances, a radiation source (506) may fire a radiation beam (508) when it is positioned a finite distance away from the detected LOR. The radiation beam (508) may be directed at a specific point (507) in the PTV (504), which may help to align the LOR (504) and the radiation beam (508). The point (507) may be the midpoint of a line segment formed by the intersection of the LOR with the PTV. For example, the point (507) may be computed by identifying a first point where the LOR crosses the boundary of a PTV, identifying a second point where the LOR crosses the boundary of the PTV at a second location of the boundary, connecting the first and second points to define a line segment. The point (507) may be the midpoint of the defined line segment. Alternatively, the point (507) may be at any another location within the PTV.

Figure 5B:
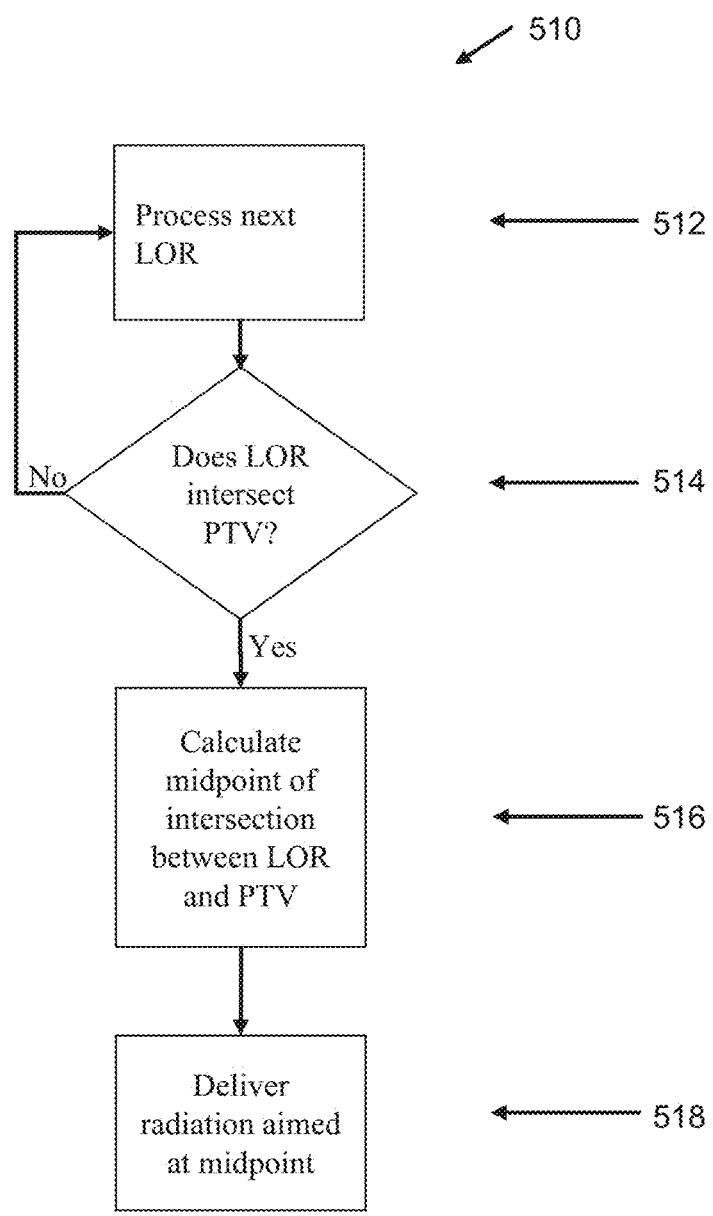
FIG. 5B is a flowchart diagram of an exemplary implementation of the method depicted in FIG. 5A.

One example of a method (510) of precisely directing a radiation beam at a particular location in a PTV is diagrammatically represented in FIG. 5B. The method (510) directs the radiation source to apply a radiation beam at the midpoint of a line segment formed by the intersection of the LOR with the PTV. This method may be implemented using an EGRT system comprising a movable gantry, one or more positron emission detectors along the gantry, one or more radiation sources along the gantry, a motion system, and a microprocessor. Processing a LOR (512) may comprise detecting a single coincident positron annihilation emission path using a positron emission detector, and may optionally comprise storing data about the LOR (e.g., location data, signal strength data, etc.) in a memory of the microprocessor. Next, the microprocessor may evaluate whether the LOR intersects a PTV (514) by comparing location data of the LOR with location data of the PTV. If not, the EGRT system may return to the initial state (512) to detect another LOR. If so, the microprocessor may compute (516) the midpoint of the line segment formed by the intersection of the LOR with the PTV. The microprocessor may then provide an instruction to the radiation source to direct and apply (518) a radiation beam toward the midpoint computed in the previous step. Once radiation has been delivered along the detected LOR, the method (510) may be repeated as may be desirable, e.g., until a prescribed dose of radiation has been applied to the PTV.

Other variations of EGRT methods may comprise delivering radiation in response to a single LOR from multiple locations and/or at multiple points in time. As an example, a radiation beam may be delivered along a LOR from either end of the LOR, or at different times front the same LOR endpoint. FIGS. 6A and 6B conceptually depict one example of how multiple radiation beams may be applied along a LOR. FIG. 6A depicts a patient (600) located in a gantry (602) with a PET-avid region of a PTV (604). A LOR (606) originating from within the PTV (604) may be detected at a first location (608) and a second location (610) along the gantry (602). A radiation source (612) may be moved along the gantry at various positions to apply a radiation beam along the LOR (606) to the PTV (604). For example, as depicted in FIG. 6B, the radiation source (612) may be moved to the first location (608) to apply a first radiation beam (614) along the LOR (606) to the PTV (604). Additionally or alternatively, as depicted in FIG. 6C, the radiation source (612) may be moved to the second location (610) to apply a second radiation beam (616) along the LOR (606) to the PTV (604). In some variations, a plurality of radiation beams may be applied from the radiation source (612) along the LOR (606) located at a single position.

Figure 6D:
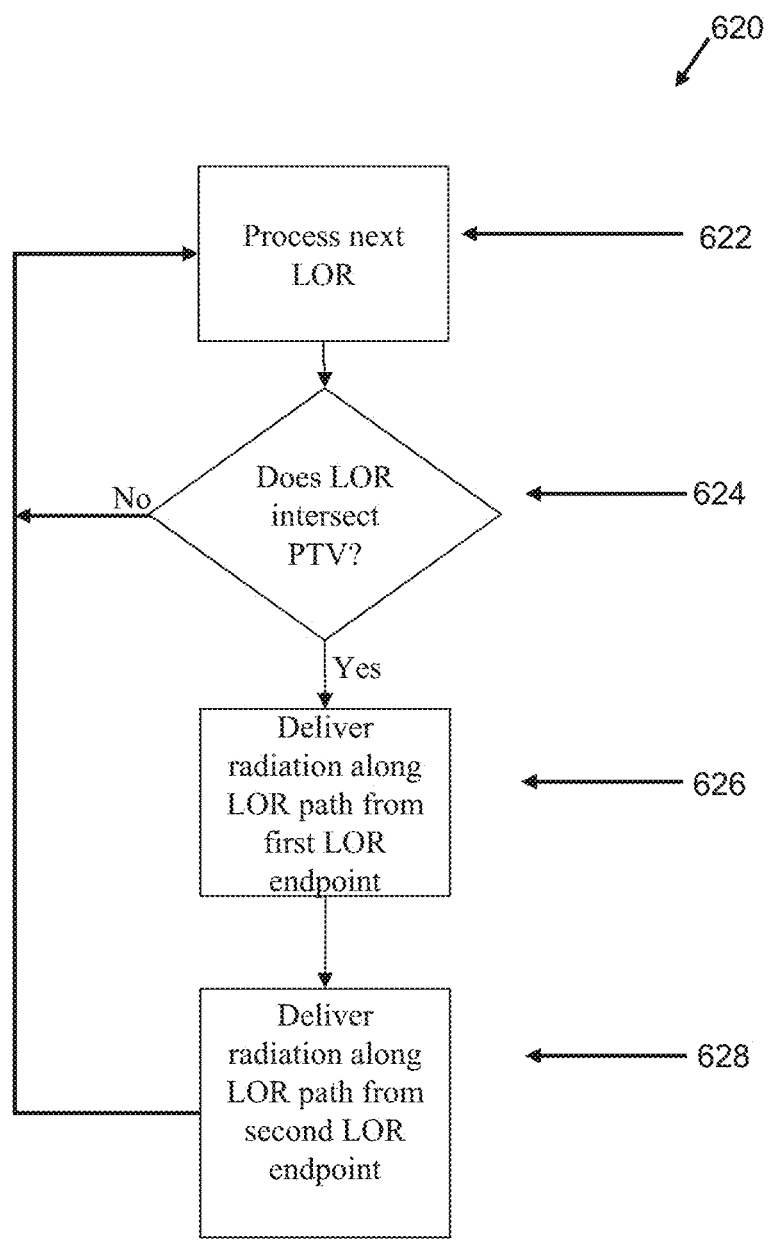
FIG. 6D is a flowchart diagram of an exemplary implementation of the method depicted in FIGS. 6A to 6C.

One example of a method (620) of precisely directing a radiation beam at a particular location in a PTV is diagrammatically represented in FIG. 6D. The method (620) directs the radiation source to apply a radiation beam from one or more endpoints of a detected LOR. This method may be implemented using an EGRT system comprising a movable gantry, one or more positron emission detectors along the gantry, one or more radiation sources along the gantry, a motion system, and a microprocessor. Processing a LOR (622) may comprise detecting a single coincident positron annihilation emission path using a positron emission detector, and may optionally comprise storing data about the LOR (e.g., location data, signal strength data, etc.) in a memory of the microprocessor. Next, the microprocessor may evaluate whether the LOR intersects a PTV (624) by comparing location data of the LOR with location data of the PTV. If not, the EGRT system may return to the initial state (622) to detect another LOR. If so, the microprocessor may provide an instruction to the radiation source to deliver (626) a first radiation beam along the LOR from a first location. The microprocessor may then provide an instruction to the radiation source to apply (628) a second radiation beam along the LOR from a second location. Optionally, a plurality of radiation beams may be delivered along the LOR from the same location. Once radiation has been delivered along the detected LOR, the method (620) may be repeated as may be desirable, e.g., until a prescribed dose of radiation has been applied to the PTV.

Another variation of a method may combine intensity modulated radiotherapy (IMRT) and EGRT to deliver radiation treatment to a planning target volume. A hybrid IMRT-EGRT method may be useful if the coincident positron annihilation emission signal is low, or if shorter treatment time is desired. In some variations, IMRT and EGRT may have separate pre-treatment plans, and during the radiation therapy, IMRT may be used to deliver radiation beams for one portion of the session, while EGRT may be used to deliver radiation beams for another portion of the session. For example, the radiation beam may be applied using IMRT first and EGRT second (or vice versa) for each position of the radiation source along the gantry. Some methods may alternate between IMRT and EGRT for one or more radiation source positions during the radiation therapy session.

Figure 7:
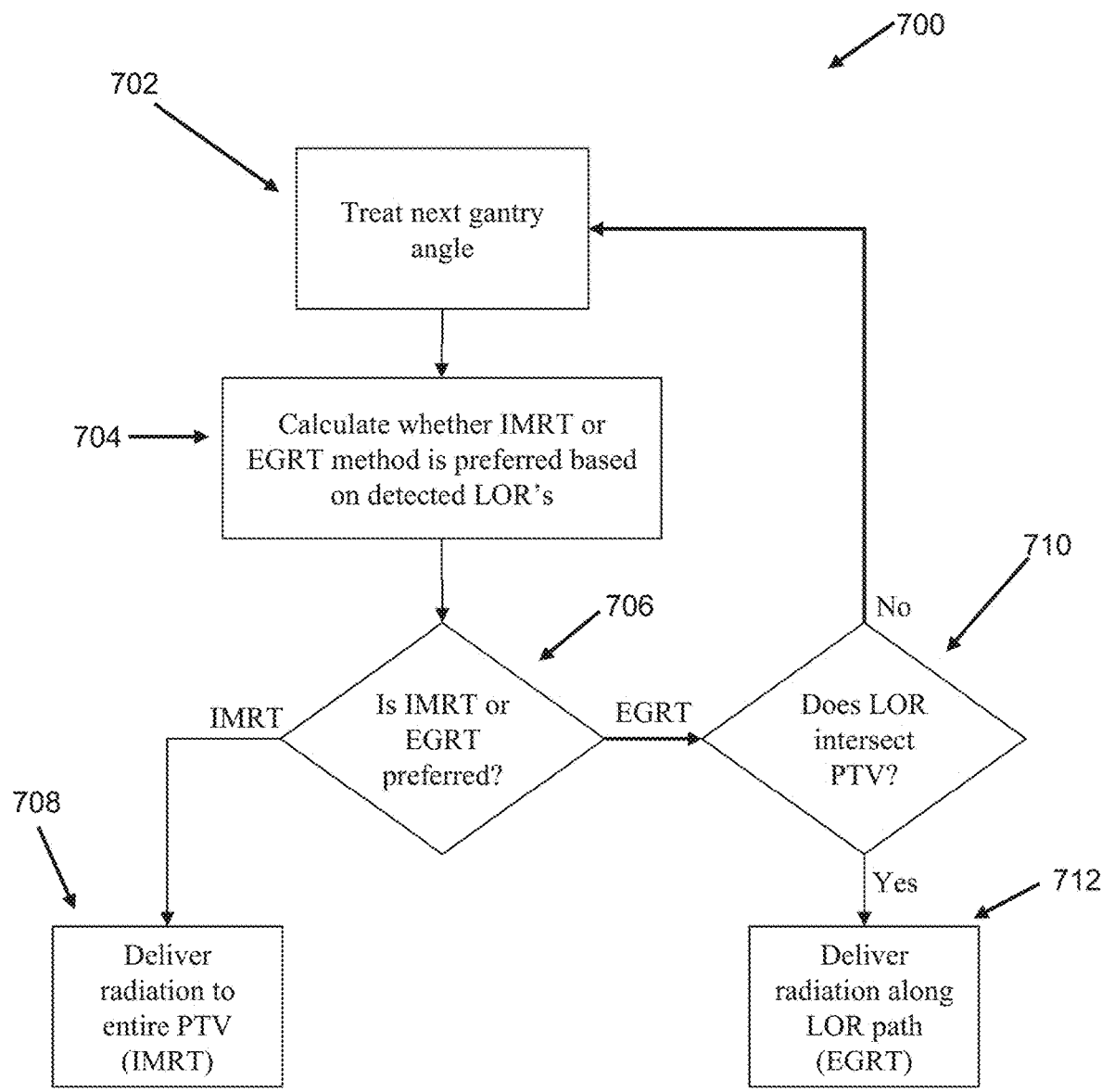
FIG. 7 is a flowchart diagram of one example of a method that uses both EGRT techniques and intensity modulated radiation therapy (IMRT) techniques.

One example of a hybrid IMRT-EGRT method (700) is diagrammatically represented in FIG. 7. The method (700) may utilize both IMRT and EGRT techniques to apply radiation to a PTV. The method (700) may be implemented using an EGRT system comprising a movable gantry, one or more positron emission detectors along the gantry, one or more radiation sources along the gantry, a motion system, and a microprocessor. The radiation source may be moved to a first location along the gantry, at a certain gantry angle (702). In some variations, the set of gantry angles may be uniformly spaced around a circular gantry, while in other variations, the spacing of the gantry angles may not be uniform. At each gantry angle location, the microprocessor may receive data regarding a plurality of LOR from the positron emission detector(s) (e.g., location data signal strength data, etc.), and may compute (704) or calculate based on a pre-programmed or pre-determined model stored in the microprocessor whether IMRT or EGRT should be used to deliver radiation to the PTV (706). This determination may be based on whether there are sufficient LOR data to respond to using EGRT. If IMRT is selected, then the microprocessor may provide an instruction to the radiation source to deliver (708) radiation to the entire PTV. If EGRT is selected, the microprocessor may evaluate whether the LOR intersects a PTV (710). If not, the EGRT system may return to the initial state (702) to treat the next gantry angle. If so, the microprocessor may provide an instruction to the radiation source to deliver (712) a radiation beam along the LOR. Once radiation has been delivered using IMRT or EGRT, the radiation source may be moved to another location, and the method (700) may be repeated as may be desirable, e.g., until a prescribed dose of radiation has been applied to the PTV.

In another variation of a method for EGRT, the method may comprise steps that update the location and/or orientation of the PTV during the treatment session. For example, the centroid of the PTV may be redefined to account for any tumor movement that may occur during the treatment (e.g., due to a change in the patient's breathing pattern, organ deformation, peristalsis, or a shift in the patient's position, etc.). FIGS. 8A and 8B conceptually depict a patient area (800) with a PTV (802) at an initial position and a tumor (804) at an initial position in the PTV (802). The initial positions of the PTV and tumor may be measured in a pre-treatment session or at an earlier point in time during the radiotherapy session. In the course of radiation therapy, the position of the PTV may need to be shifted, for example, to the position depicted in FIG. 8B. As illustrated there, the PTV may be redefined to a second position (806) to reflect the tumor's (808) new range of motion. In some examples, the centroid of the PTV may be redefined according to an average range of motion of the tumor. Additionally or alternatively, PET images may be reconstructed based on the PET signal data in a previous time interval (e.g., the last 0.5 s, 1 s, 2 s, 10 s, 20 s, 50 s, 60 s, 90 s, etc.) and used to transform (translate, rotate, reorient, stretch or shrink, etc.) the PTV. Some EGRT methods may comprise a step to redefine the PTV centroid based on a change in the centroid of the temporally-blurred reconstructed PET image relative to the baseline scan or relative to the last reconstructed PET image.

Figure 8C:
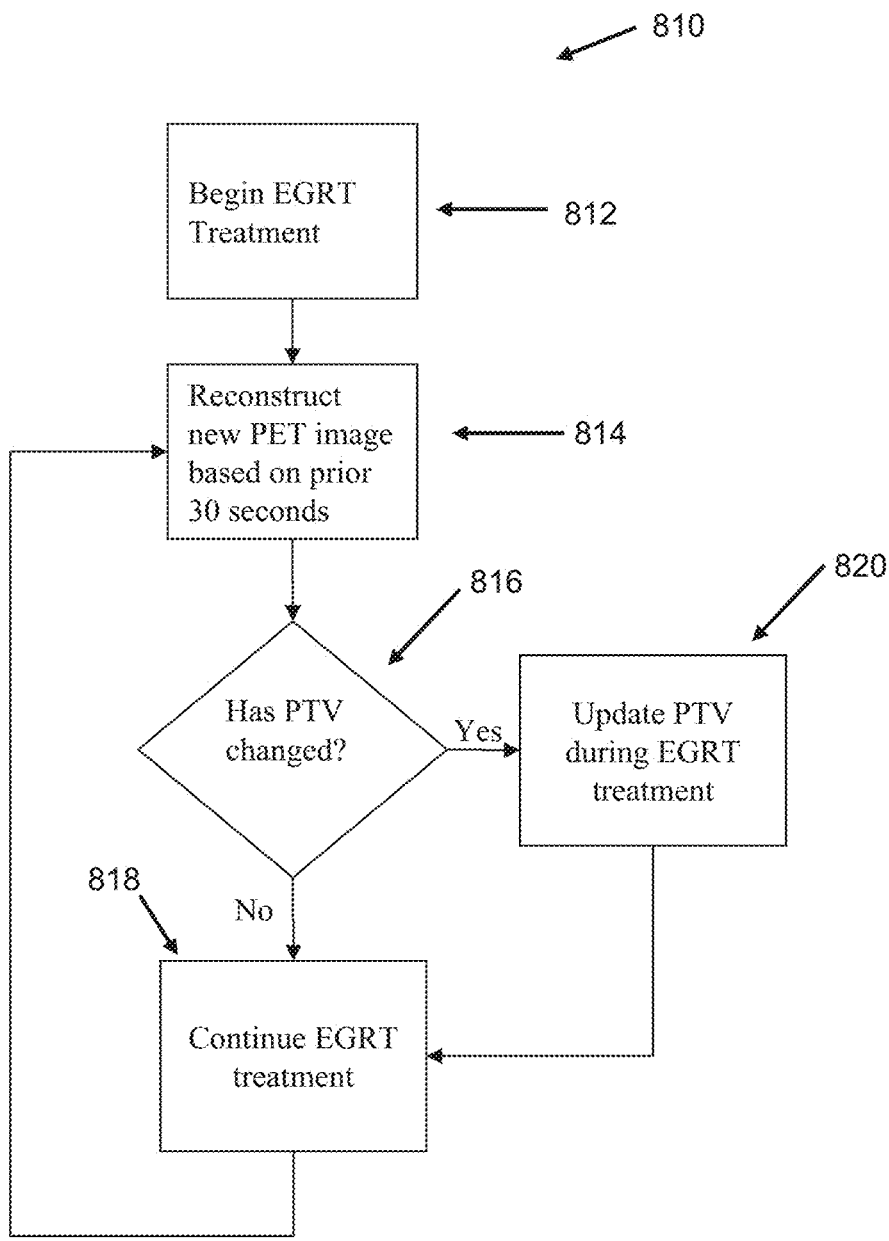
FIG. 8C is a flowchart diagram of an exemplary implementation of the method depicted in FIGS. 8A and 8B.

One example of an EGRT method (810) that periodically updates the position of the PTV is depicted in FIG. 8C. The method (810) may update the position of the PTV every 30 seconds, but it should be understood that any update period may be selected as desired (e.g., 0.5 s, 1 s, 2 s, 10 s, 20 s, 50 s, 60 s, 90 s, etc.). The method (810) may be implemented using an EGRT system comprising a movable gantry, one or more positron emission detectors along the gantry, one or more radiation sources along the gantry, a motion system, and a microprocessor. After the start of the EGRT treatment (812), the microprocessor may reconstruct (814) an initial or new PET image based on pre-treatment data or recent positron annihilation emission data from the last 30 seconds. The PET data and/or image may be stored in a memory of the microprocessor. The microprocessor may then determine (816) whether the current position of the PTV has changed from the previous position of the PTV by comparing location data of the current position of the PTV with location data of the previous position of the PTV. If not, the microprocessor may provide an instruction to the radiation source to apply a radiation beam along a detected LOR, as previously described, and EGRT may then resume (818). If so, the PTV position may be updated (820) in the memory of the microprocessor. The microprocessor may then use the updated PTV location information to determine whether detected the LOR are located within the updated PTV. EGRT may resume (818). Once radiation has been delivered along the LOR the method (810) may be repeated as may be desirable, e.g., until a prescribed dose of radiation has been applied to the PTV.

Figure 9A:
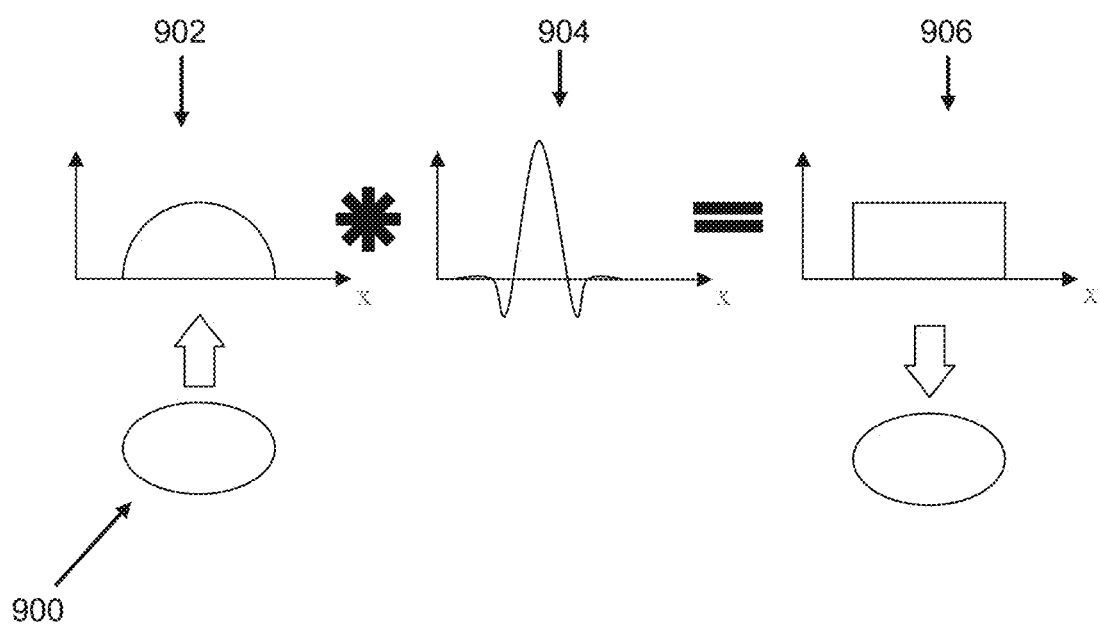
FIG. 9A is a conceptual depiction of another example of an EGRT method for modulating the radiation applied to a PTV for uniform dose distribution.

Some variations of EGRT methods may be used to reduce or avoid the peaking of a radiation dose that may occur in the center of an otherwise uniformly PET-avid volume (i.e., "backprojection effect"). This effect may occur because LOR that intersect the volume near the center of the PET-avid volume may be detected more frequently than those that intersect towards the edge of the volume. An EGRT method may use a filtered-backprojection technique to reduce or eliminate radiation peaks in a PET-avid region. FIG. 9A conceptually depicts one method that may be used to compute a one-dimensional mathematical projection (902) of a PET-avid volume (900) that may emit photons in a generally uniform density, and where the projection (902) is calculated by counting the number of coincident positron annihilation emissions that intersect a certain position of the radiation source. The calculated mathematical projection (902) may be mathematically filtered with a filter (904) that is appropriate for use in a filtered-backprojection algorithm, for example, a Ram-Lak filter, a Shepp-Logan filter, or any other filter that may be used for image-reconstruction. The result of the filtered projection may result in negative values which can be rectified, e.g., set to zero, to obtain a post-littered projection (906). The post-filtered projection (906) may then be used to modulate the radiation beam so that a more uniform application of radiation energy to the PET-avid volume is delivered. For example, the intensity of the delivered radiation, and/or the temporal aspect of the delivered radiation, may be proportional to the post-filtered projection (906).

Figure 9B:
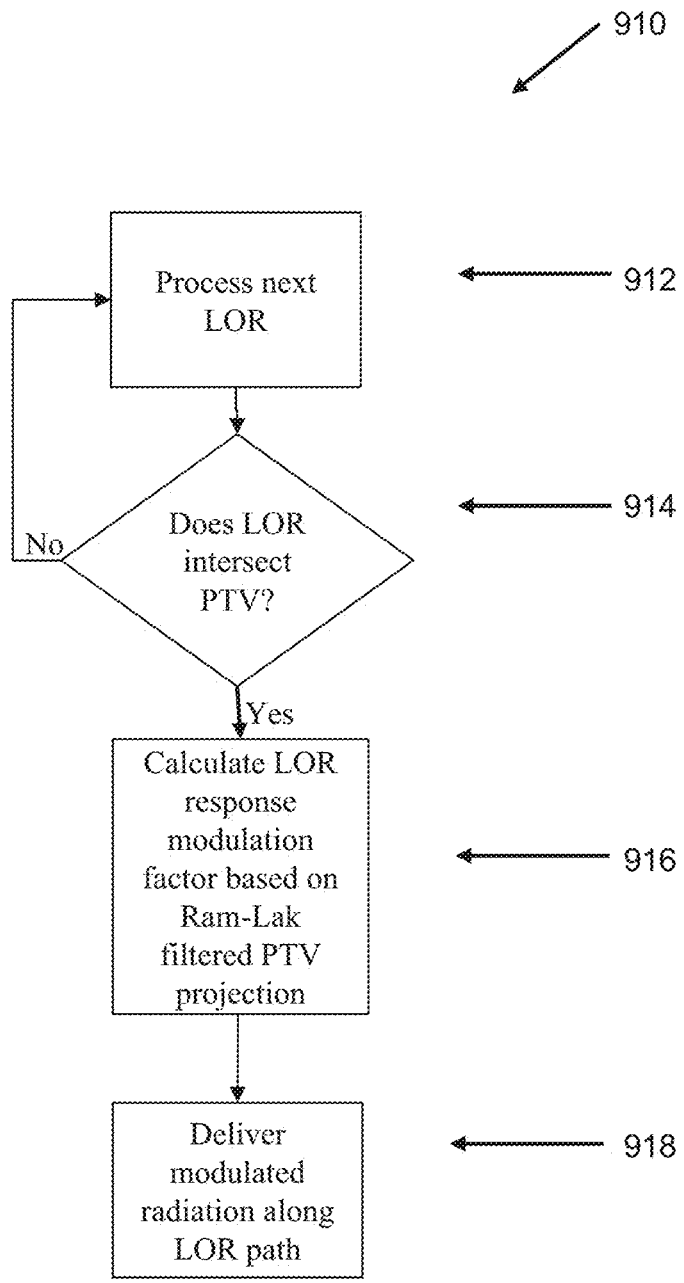
FIG. 9B is a flowchart diagram of an exemplary implementation of the method depicted in FIG. 9A.

One example of an EGRT method (910) that may be used to apply radiation that reduces or eliminates radiation peaks in a PET-avid region is depicted in FIG. 9B. This method may be implemented using an EGRT system comprising a movable gantry, one or more positron emission detectors along the gantry, one or more radiation sources along the gantry, a motion system, and a microprocessor. Processing, a LOR (912) may comprise detecting a single coincident positron annihilation emission path using a positron emission detector, and may optionally comprise storing data about the LOR (e.g., location data, signal strength data, etc.) in a memory of the microprocessor. Next, the microprocessor may evaluate whether the LOR intersects a PTV (914). If not, the EGRT system may return to the initial state (912) to detect another LOR. If so, the microprocessor calculates (916) the degree to which the radiation response to the LOR should be modulated. The microprocessor may compute a dose distribution as described in FIG. 9A, and modulate the radiation response based on a Ram-Lak filtered PTV projection, with negative values rectified to zero. The microprocessor may then provide an instruction to the radiation source to modulate the radiation beam according to the post-filtered projection. The radiation source may then deliver (918) the modulated radiation along the LOR. Once radiation has been delivered along the detected LOR, the method (910) may be repeated as may be desirable, e.g., until a prescribed dose of radiation has been applied to the PTV.

Figure 11A:
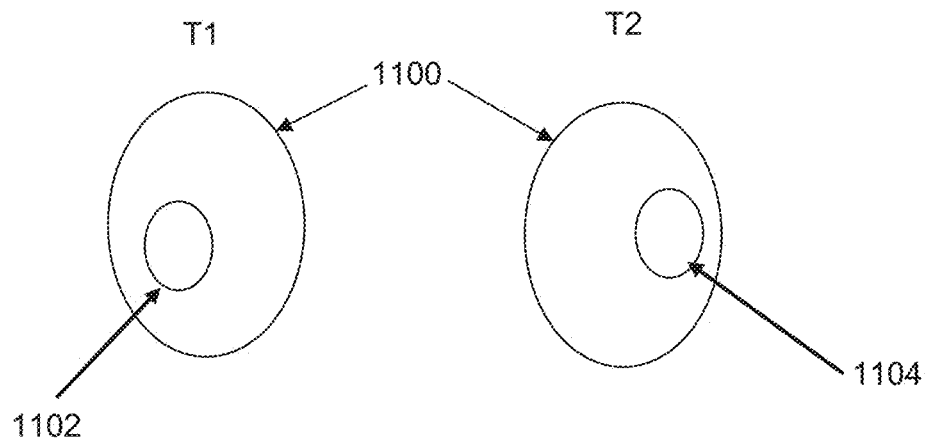
FIG. 11A is a conceptual depiction of one variation of an EGRT method for delivering radiation to a hypoxic tissue region.

Another method that may be used in EGRT may deliver a radiation dose that is proportional to the real-time or near real-time measured intensity of the positron emitting distribution or a photon emitting distribution across the patient volume to be treated. Such a method may be used with an EGRT system having positron emission and/or single-photon emission detectors to detect emission paths, and a radiation source with a collimator to shape the radiation beam applied to the PTV. The distribution of coincident positron annihilation emission and/or SPECT signals may be correlated with areas of hypoxia, increased cellular proliferation, or other biological or functional aspects of a patient volume to treated. For example, as depicted in FIG. 11A, at a particular time (T1), a tumor (1100) may have a sub-region (1102) at a first location that may demonstrate an increased rate of radiotracer uptake. The tumor and/or the sub-region may move such that the sub-region (1104) at a time (T2) may be at a second location in the tumor (1100). In some cases, it may be desirable to escalate the radiation dose to these sub-regions of the patient volume, which may involve tracking the motion of these sub-regions. Some variations of this method may use one or more PET tracers such as FDG, FLT, F-ACBC, Cu-ATSM. etc., as well as one or more SPECT tracers such as Tc-99m-tagged compounds, 99mTc-HL91, 111In-Capromab pendetide, etc., which may provide additional information about biological and functional makeup throughout the PTV.

Figure 11B:
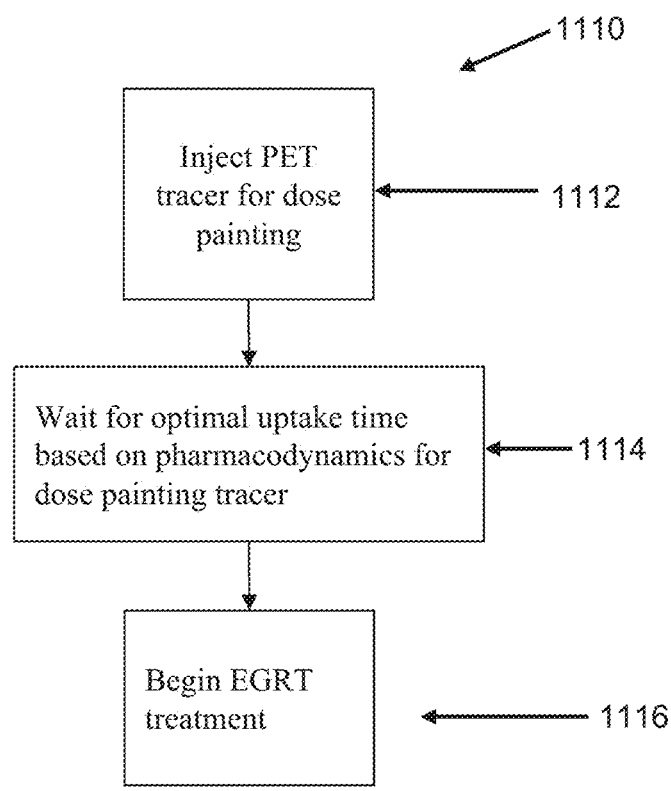
FIG. 11B is a flowchart diagram of an exemplary implementation of the method depicted in FIG. 11A.

One example of an EGRT method (1110) that delivers radiation to the PTV that is proportional to the SPECT and/or coincident positron annihilation emission signal(s) from the PTV is depicted in FIG. 11B. This method may be implemented using an EGRT system comprising a movable gantry, one or more single-photon/positron emission detectors along the gantry, one or more radiation sources along the gantry, a motion system, and a microprocessor. A SPECT or PET tracer may be injected (1112) into a patient. Examples of PET tracers that may be injected include F-MISO, FLT, FDG, etc. Examples of SPECT tracers that may be injected include Tc-99m-tagged compounds, 99mTc-HL91, 111In-Capromab pendetide (ProstaScint). After a sufficient period of time has elapsed (1114) in accordance with the pharmacodynamics for the SPECT or PET tracer, EGRT may commence (1116), as described above.

The method depicted in FIG. 11B may also be performed using SPECT tracers. An EGRT system may comprise single-photon emission detectors to capture single photons emitted from the target volume. The radiation source may then be instructed by the microprocessor to apply radiation along the linear path of the single photon-emission. The microprocessor may also discriminate between energy levels of the detected photon and modulate the level of radiation applied along the linear path of the detected photon according to the energy of the photon. In the case of PET tracers, one example of EGRT may use positron emission detectors to capture LOR emissions generated from multiple PET tracers that are within the target volume. The microprocessor will instruct the radiation source to apply radiation along detected LOR intersecting with the planning target volume.

Figure 12A:
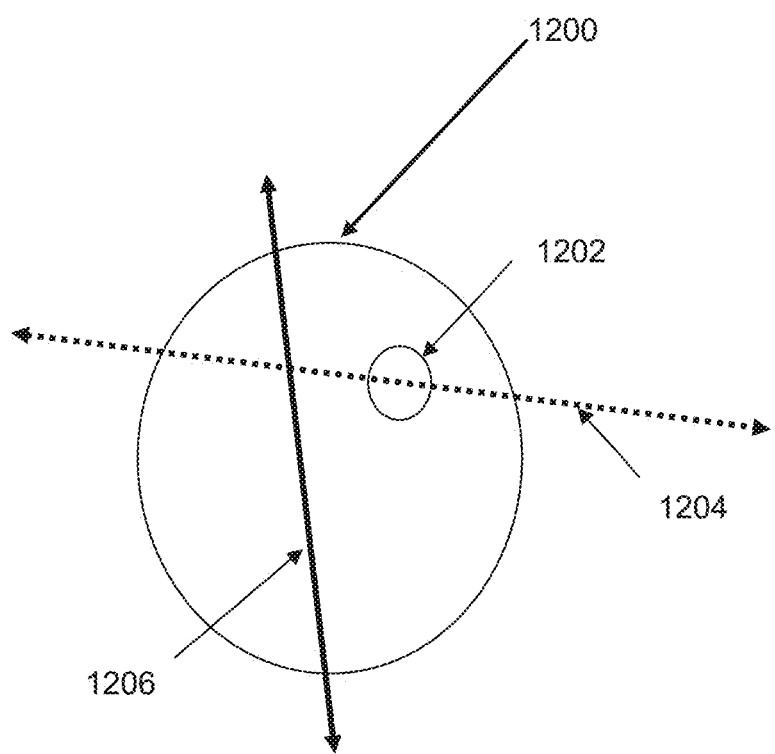
FIG. 12A is a conceptual depiction of a variation of an EGRT method for delivering radiation along a LOR that intersects a PTV with reduced positron emission activity.

In some circumstances, the PTV may have a lower LOR signal than the tissue immediately surrounding it. In such conditions, radiation beam may instead be directed to a "cold spot," which may be a region of tissue that have a lower number of detected LOR than the average rate for the surrounding tissue. A "cold spot" may be detected from a previous PET scan or by reconstructing an image using PET data accumulated over certain time intervals, (e.g., 0.5 s, 1 s, 5 s, 20 s, 30 s, 90 s before applying the radiation beam) and using the reconstructed image to determine the "cold spot" region. FIG. 12A schematically depicts a planning target volume (1200) with a "cold spot" (1.202), i.e., a region of tissue in the PTV with reduced coincident positron annihilation emission activity. Examples of "cold spot" tissues may include a region in the brain with hypo-intense FDG uptake or areas using PET tracers that detect cell apoptosis, such as 18F-ML-10. A lower density of LOR may be detected along the direction (1204), while a higher density of LOR may be detected along the direction (1206). An EGRT system may be programmed to deliver more radiation along the direction (1204) to treat the tissue within the "cold spot" (1202).

Figure 12B:
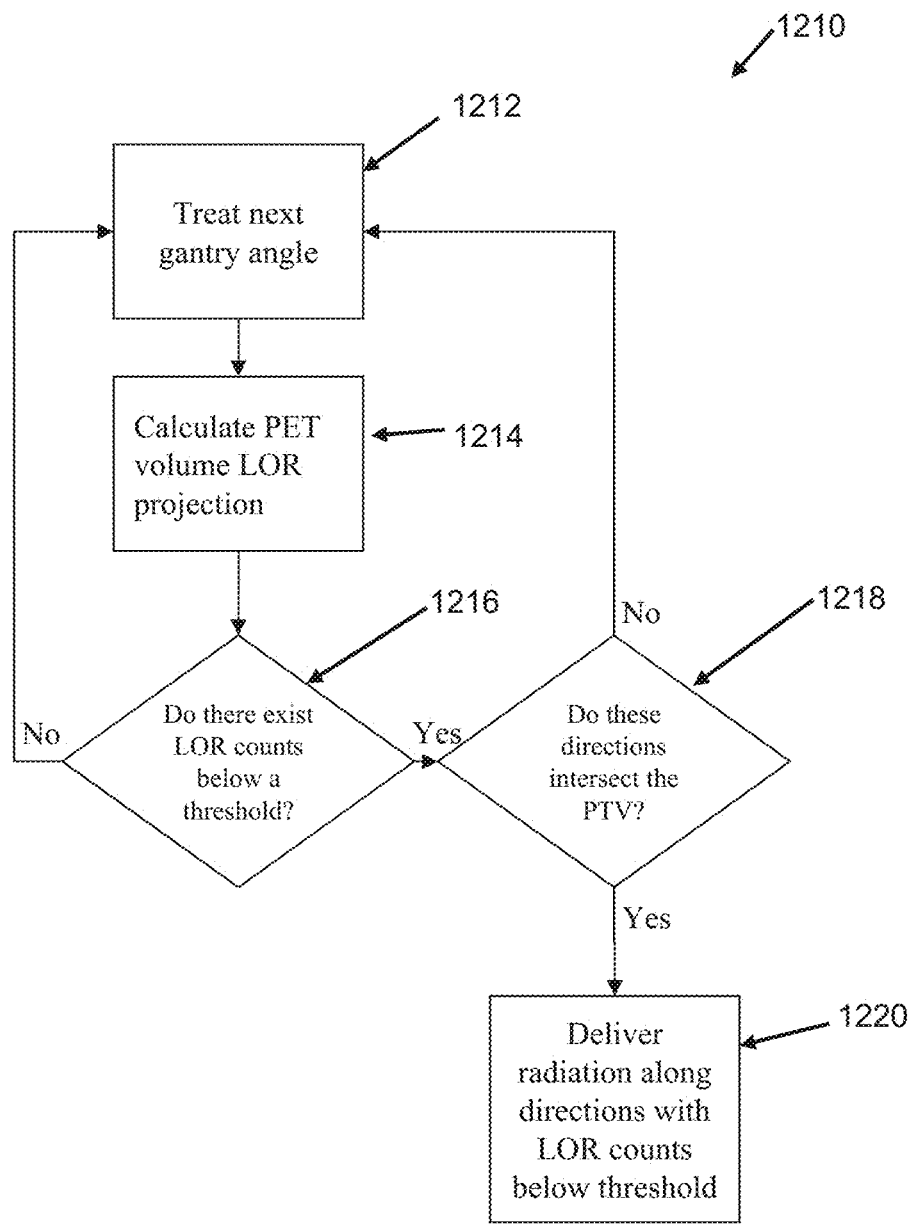
FIG. 12B is a flowchart diagram of an exemplary implementation of the method depicted in FIG. 12A.

One example of a method that may be used with an EGRT system to apply radiation to a region of tissue with low LOR activity is represented in FIG. 12B. This method may be implemented using an EGRT system comprising a movable gantry, one or more positron emission detectors along the gantry, one or more radiation sources along the gantry, a motion system, and a microprocessor. A radiation source may be positioned at a certain location on the gantry (1212). The microprocessor may use data collected from the one or more positron emission detectors to calculate (1214) a PET volume LOR projection at the location of the radiation source. The microprocessor then compares (1216) the LOR counts with a pre-determined threshold, which may be determined from a previously stored image, such as a prior PET scan image, or by reconstructing an image using PET data accumulated over a prior time interval. If the LOR counts are above the pre-determined threshold, the microprocessor does not issue an instruction to fire a radiation beam, and the EGRT system may return to the initial state (1212) to process the LOR projection at another gantry location. If the LOR counts are below the pre-determined threshold, the microprocessor may evaluate whether the direction(s) of the LOR intersect the PTV (1218). If the direction(s) of the LOR do not intersect the PTV, the microprocessor does not issue an instruction to fire a radiation beam, and the EGRT system may return to the initial state (1212) to process the LOR projection at another gantry location. If the direction(s) of the LOR intersect with the PTV, the microprocessor may provide an instruction to the radiation source to deliver (1220) radiation along the direction(s) where the LOR counts are below the pre-determined threshold. The method depicted in FIG. 12B may also be performed using SPECT tracers and an EGRT system comprising single-photon emission detectors.

Optionally, any of the methods above may use multiple radioactive tracers at once, such as PET or SPECT radiotracers. For example, a patient may be injected with a cocktail of FDG and FLT, or any other desired combination radioactive tracers. The EGRT system may be configured to apply a radiation beam along any detected LOR that intersects with the PTV, regardless of which type of tracer originated the decay event.

Figure 13:
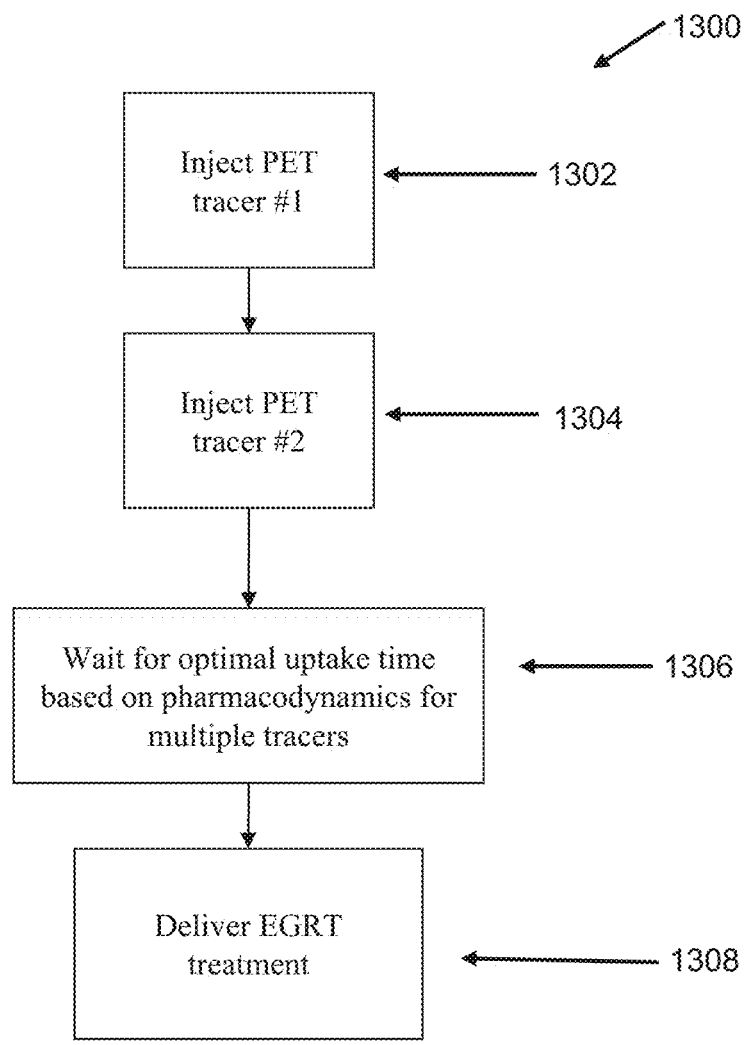
FIG. 13 is a flowchart diagram of one example of an EGRT method that uses more than one PET tracer.

One method (1300) in which multiple PET tracers may be used with any of the EGRT methods described herein is depicted in FIG. 13. This method may be implemented using an EGRT system comprising a movable gantry, one or more positron emission detectors along the gantry, one or more radiation sources along the gantry, a motion system, and a microprocessor. A first tracer (e.g., FDG) may be injected (1302) into a patient. Subsequently or simultaneously, a second tracer (e.g., FLT) may be injected (1304) into the patient. After a sufficient period of time has elapsed (1306) in accordance with the pharmacodynamics for the first and second tracers, EGRT may commence (1308), as previously described.

Additionally, any of the methods described above may be used in combination with a fiducial marker, radiopaque marker, or any other identifier that allows the PTV to be tracked for radiation therapy. In some variations, the methods described herein may be used in combination with surgery and/or chemotherapy, as may be appropriate.

Figure 10A:
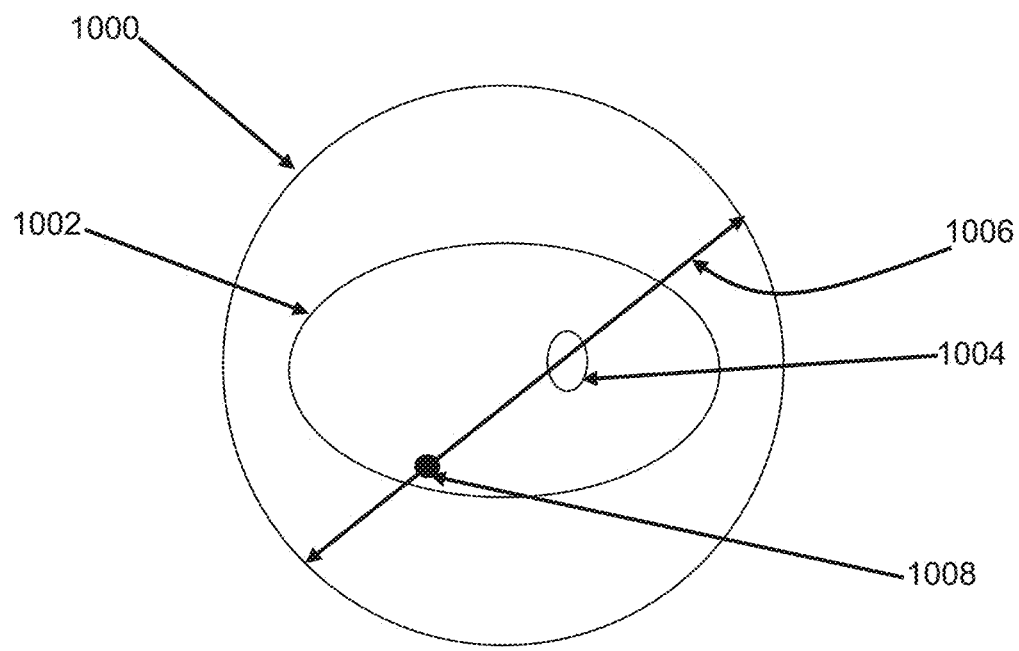
FIGS. 10A and 10B are conceptual depictions of an EGRT method for calculating the origin point of a LOR.
Figure 10B:
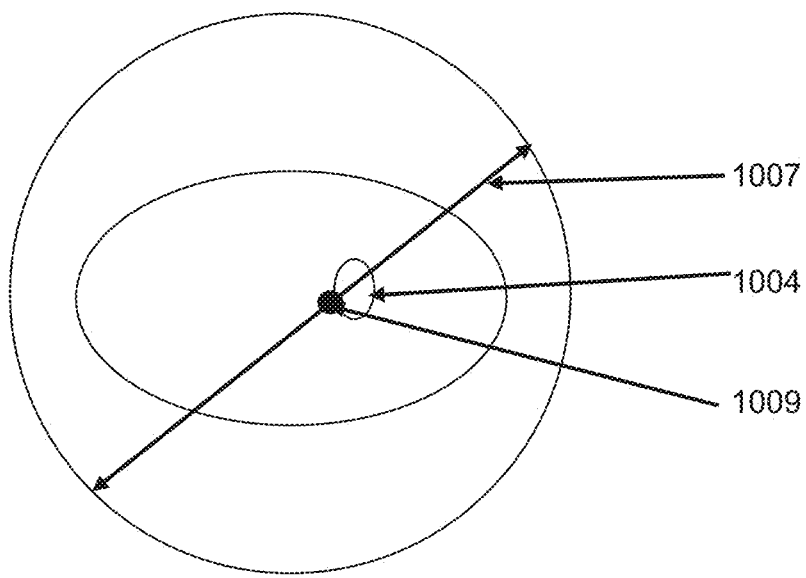

Optionally, any of the methods described above may use the time-of-flight (TOF) method to evaluate whether the origin of a positron annihilation emission is within, or sufficiently close to, a planning target volume. The TOF method may be used with a PET system to help improve diagnostic PET image quality by calculating the time difference between the detection of each endpoint of a single LOR (i.e. the time difference between the detection of each of the coincident positron annihilation emission photons). Using information obtained from the TOF method, a microprocessor may estimate or computer the origin point of the positron emission along the LOR path. For example, a method with an estimation error of the origin point on the order of 5 cm may trigger the system to exclude LOR events whose calculated positron emission origin points are greater than this error (e.g. 5 cm) from the PTV boundary. FIGS. 10A and 10B conceptually depict how the TOF method may be used with any of the EGRT systems and methods described above. A patient (1002) located within a gantry (1000) may have a PTV (1004). The EGRT system may detect a LOR (1006), and the microprocessor of the EGRT may use the TOF method to evaluate whether the origin point of the LOR is within, or sufficiently close to, the PTV. For example, in FIG. 10A, the calculated origin point (1008) of a LOR (1006) is shown. Since the origin point (1008) does not co-localize with the PTV (1004), and is not sufficiently close to the PTV (1004), the microprocessor may be programmed to disregard the LOR (1006), return to a state to process a new LOR. Another example depicted in FIG. 10B depicts an example where the calculated origin point (1009) of the LOR (1007) is sufficiently close to the PTV, and the microprocessor may be programmed to provide an instruction to the radiation source to apply radiation along the LOR (1007). Including the TOF method in combination with any of the EGRT systems described above may help to improve EGRT performance by excluding events that did not originate from within, or are sufficiently close to, the PTV.

Figure 10C:
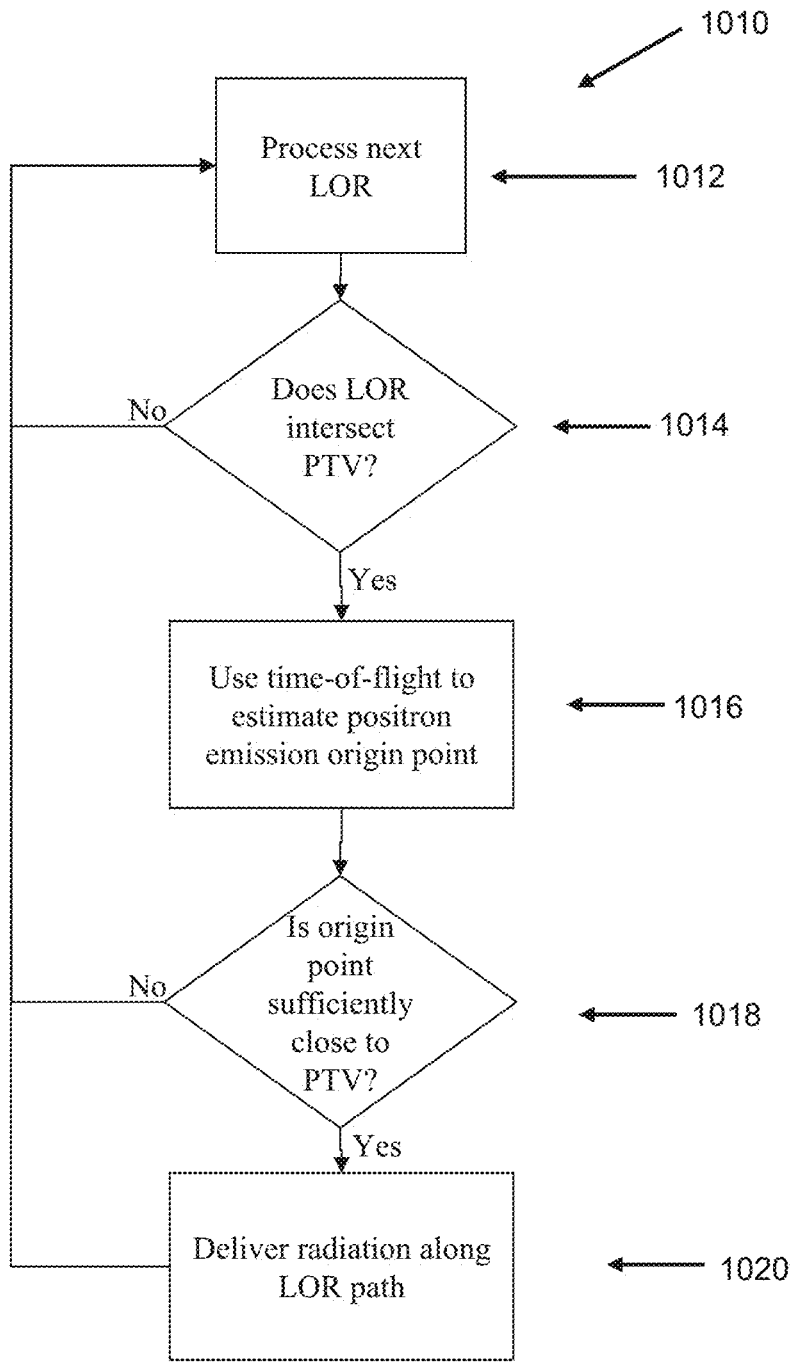
FIG. 10C is a flowchart diagram of an exemplary implementation of the method depicted in FIG. 10A.

One example of the TOF method (1010) that may be used with any of the EGRT methods described above is depicted in FIG. 10C. This method may be implemented using an EGRT system comprising a movable gantry, one or more positron emission detectors along the gantry, one or more radiation sources along the gantry, a motion system, and a microprocessor. Processing a LOR (1012) may comprise detecting a single coincident positron annihilation emission path using a positron emission detector, and may optionally comprise storing data about the LOR (e.g., location data, signal strength data, etc.) in a memory of the microprocessor. Next, the microprocessor may evaluate whether the LOR intersects a PTV (1014) by comparing location data of the LOR with location data of the PTV. If not, the EGRT system may return to the initial state (1012) to detect another LOR. If so, the microprocessor uses the TOF method to computer the positron emission origin point (1016). Based on the location of the origin point with respect to the PTV, the microprocessor may then evaluate whether the origin point is sufficiently close to the PTV (1018). If not, then the EGRT system may return to the initial state (1012) to detect another LOR. If so, then the microprocessor may then provide an instruction to the radiation source to deliver (1020) radiation along the LOR. Once radiation has been delivered along the detected LOR, the method (1010) may be repeated as may be desirable, e.g., until a prescribed dose of radiation has been applied to the PTV.

Figure 15A:
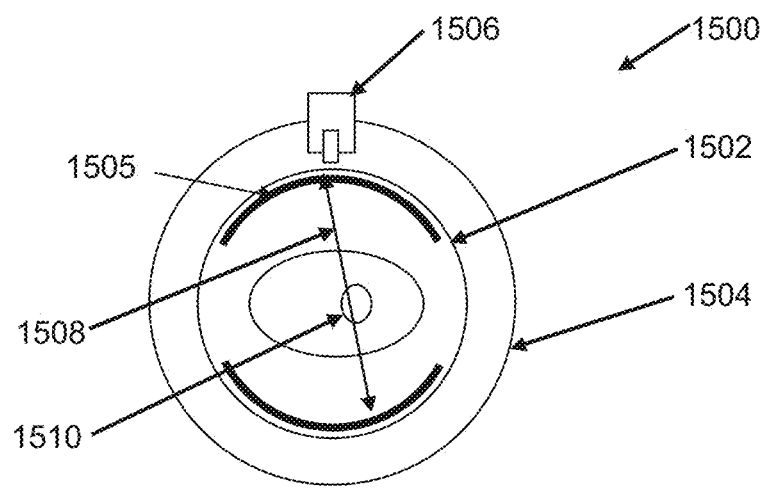
FIG. 15A to 15B is a schematic depiction of an example of an EGRT system with a movable inner gantry and a separately movable outer gantry.
Figure 15B:
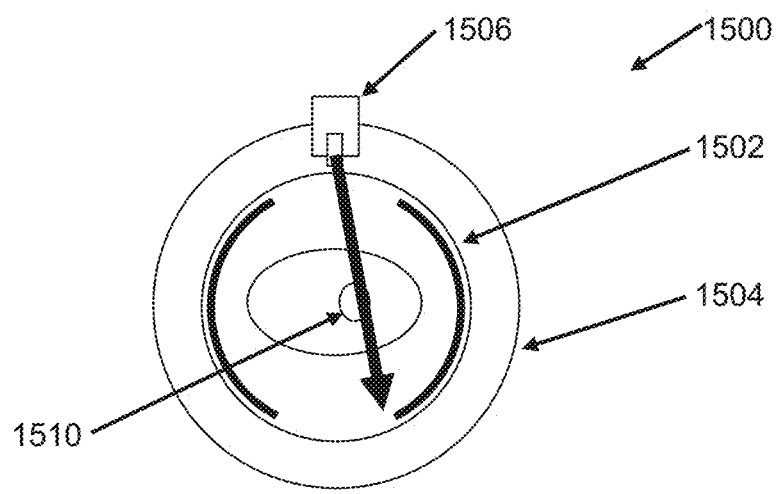

As indicated previously, any of the above methods may be performed using any suitable EGRT system, for example, such as the EGRT systems described in U.S. Pat. Appl. Publ. No. 2009/0256078 filed on Feb. 9, 2009, which was previously incorporated by reference in its entirety. Another variation of an EGRT system that combines PET with radiotherapy may comprise a gantry having an inner gantry and an outer gantry that are each separately rotatable. One or more positron emission detectors may be located on the inner gantry, while one or more radiation sources may be located on the outer gantry. The inner gantry may rotate at a faster rate than the outer gantry. In some variations, the inner gantry with the positron emission detectors may rotate faster than the outer gantry with the radiation source because the positron emission detectors may weigh less than the radiation source. Alternatively or additionally, the inner and outer gantries may each be supported by motor systems with different power outputs, where each of the motor systems may be independently controlled. FIGS. 15A and 15B depict one example of an EGRT system (1500). The inner gantry (1502) has two positron emission detectors (1505) located 180 degrees across from each other. The outer gantry (1504) has a radiation source (1506) configured to respond to a LOR (1508) that intersects a PTV (1510). The EGRT system may have a first mode (e.g., "sense" mode) where the EGRT system detects one or more LOR, and a second mode (e.g., "fire" mode) where the EGRT applies radiation along the detected LOR that intersects the PTV (1510). In the sense mode, the positron emission detectors may occlude the subject from the radiation source (1506), as depicted in FIG. 15A. In the sense mode, lines of response may be detected, but no radiation is delivered. In the fire mode depicted in FIG. 15B, the positron emission detectors no longer occlude the patient from the radiation source and the radiation source (1506) may apply radiation along the detected LOR. The inner gantry (1502) supporting the positron emission detectors may be able to rotate substantially faster than the outer gantry (1504) supporting the radiation source, which may allow for very small lag times between LOR detection and radiation response.

Figure 15C:
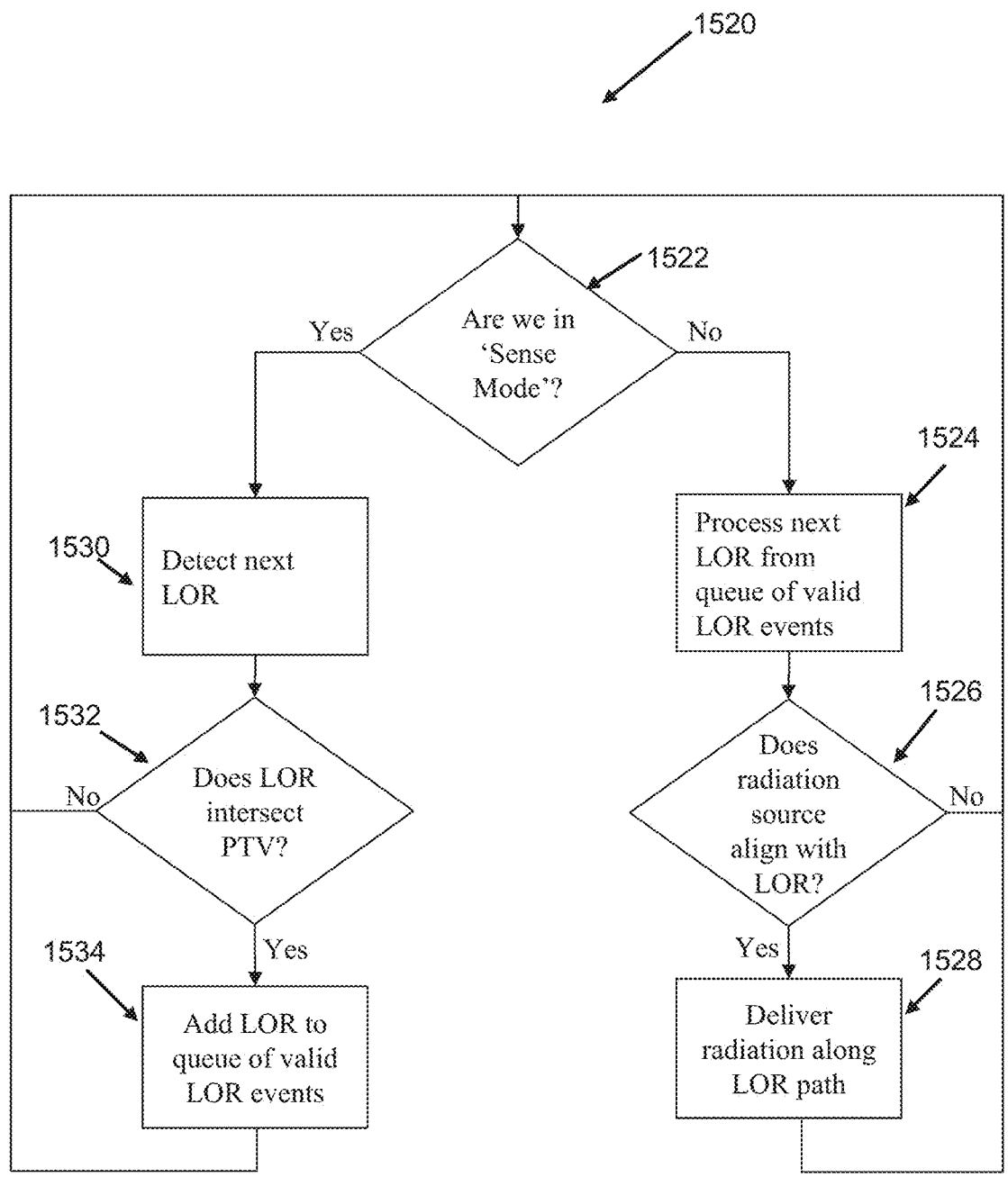
FIG. 15C is a flowchart diagram of one example of how the system depicted in FIGS. 15A and 15B may be used.

One example of a method that may be used with an EGRT system comprising a gantry with separately rotatable inner and outer gantries, one or more positron emission detectors along the gantry, one or more radiation sources mounted on the gantry, a motion system, and a microprocessor, is represented in FIG. 15C. The microprocessor may first determine, based on user input and/or a pre-programmed state, whether the system is in sense mode (1522). If the EGRT system is in sense mode, LOR measured by the positron emission detectors (1530) may be collected and optionally stored in a memory of the positron emission detector and/or microprocessor. The microprocessor may compare the orientation and direction of the LOR with the location of the PTV, and determine whether the LOR intersects the PTV (1532). If the LOR does not intersect the PTV, the microprocessor may return to the initial state (1522). If the LOR does intersect the PTV, the LOR is added to a memory queue of the microprocessor (1534). A plurality of LOR may be stored in the memory queue while the EGRT system is in sense mode. In some variations, the EGRT system may initialize into sense mode at the start of a radiation therapy session.

However, if in the initial state (1522), the microprocessor determines that the EGRT system is not in sense mode, or if the microprocessor may process a line of response from a queue of valid lines of response (1524). Processing a LOR may comprise detecting a single coincident positron annihilation emission path using the positron emission detectors, and may optionally comprise storing data about the LOR in a memory queue of the microprocessor. The microprocessor may then compare the location of the LOR with the location of the radiation source, e.g., by querying the radiation source, to determine whether the radiation source is generally aligned with the LOR (1526). If not, then the microprocessor may not provide an instruction to the radiation source to apply radiation along the LOR, and return to the initial state (1522). If so, then the microprocessor may provide an instruction to the radiation source to fire a radiation beam along the LOR (1528). This may be repeated until the system is returned to sense mode, or until radiation has been delivered along all the LOR stored in the memory queue.

Although the foregoing invention has, for the purpose of clarity and understanding been described in some detail by way of illustration and example, it will be apparent that certain changes and modifications may be practiced, and are intended to fall within the scope of the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. For all the embodiments described herein, the steps of the method need not be performed sequentially.

What is claimed as new and desired to be protected is:

1. A system for positioning a radiation source comprising:
    a gantry;
    a radiation source mounted on the gantry;
    positron emission detectors mounted on the gantry, wherein the positron emission detectors are configured to detect a positron annihilation emission path; and
    a controller in communication with the radiation source and the positron emission detectors, the controller configured to
    determine whether the detected emission path intersects a first PET-avid region of interest and a second PET-avid region of interest within a coordinate system, and
    if it is determined that the emission path intersects a first PET-avid region of interest and a second PET-avid region of interest, position the radiation source with respect to the emission path at a location, wherein the radiation source is configured to generate radiation that is adjusted according to a modulation factor computed based on a projection of the first PET-avid region of interest on the location of the radiation source.

2. The system of claim 1, wherein the radiation source is configured to generate a radiation beam with a time duration that is adjusted by the modulation factor.

3. The system of claim 1, wherein the radiation source is configured to generate radiation with an intensity that is adjusted by the modulation factor.

4. The system of claim 1, wherein the second PET-avid region of interest intersects with a third region of interest, and the first region of interest does not intersect with the third region of interest.

5. The system of claim 1, wherein the second PET-avid region of interest is located within a planning target volume and the first PET-avid region of interest is located outside the planning target volume.

6. The system of claim 1, wherein the modulation factor is inversely proportional to the projection of the first PET-avid region of interest on the location of the radiation source.

7. The system of claim 1, wherein positioning the radiation source comprises aligning the radiation source along the emission path.

8. The system of claim 1, wherein the detected positron annihilation emission path is defined by a pair of photons emitted by a positron annihilation event, and the controller is further configured to
    calculate a time difference between the detection of each of the photons in the pair of photons,
    calculate a location of the positron annihilation event based on the calculated time difference, wherein the location calculation has an estimation error,
    determine whether the location of the positron annihilation event is within the estimation error from a boundary of the first PET-avid region of interest, and
    send an instruction to the radiation source to generate radiation to the first PET-avid region of interest that is adjusted according to the modulation factor if the location of the positron annihilation event is within the estimation error from the boundary of the first PET-avid region of interest.

9. The system of claim 1, wherein the radiation source is configured to generate radiation having a number of radiation firings, wherein the number of radiation firings is adjusted by the modulation factor.

10. The system of claim 1, wherein the radiation source is configured to generate radiation having a radiation beam with a duty cycle that is adjusted by the modulation factor.

* * * * *